(12) United States Patent
Mulinti et al.

(10) Patent No.: US 11,622,723 B2
(45) Date of Patent: Apr. 11, 2023

(54) SYSTEMS AND METHODS FOR PHYSIOLOGICAL SIGNAL COLLECTION

(71) Applicant: LIFESIGNALS, INC., Fremont, CA (US)

(72) Inventors: Raghavendra Mulinti, Bangalore (IN); Krishna Sankar Madhavan Pillai, Bangalore (IN); Guruprasad Shimoga Revanna, Bangalore (IN); Surendar Magar, Dublin, CA (US)

(73) Assignee: LIFESIGNALS, INC., Fremont, CA (US)

( * ) Notice: Subject to any disclaimer, the term of this patent is extended or adjusted under 35 U.S.C. 154(b) by 1168 days.

(21) Appl. No.: 16/131,294

(22) Filed: Sep. 14, 2018

(65) Prior Publication Data
US 2019/0099132 A1    Apr. 4, 2019

Related U.S. Application Data

(63) Continuation of application No. PCT/US2017/023601, filed on Mar. 22, 2017.
(Continued)

(51) Int. Cl.
*A61B 5/00*    (2006.01)
*A61B 5/024*    (2006.01)
(Continued)

(52) U.S. Cl.
CPC .......... *A61B 5/6833* (2013.01); *A61B 5/0006* (2013.01); *A61B 5/0022* (2013.01);
(Continued)

(58) Field of Classification Search
CPC ... A61B 5/6833; A61B 5/0006; A61B 5/0022; A61B 5/02433; A61B 5/0245;
(Continued)

(56) References Cited

U.S. PATENT DOCUMENTS

| 3,786,391 A | 1/1974 | Mathauser |
| 3,808,577 A | 4/1974 | Mathauser |

(Continued)

FOREIGN PATENT DOCUMENTS

| CN | 101534706 A | 9/2009 |
| CN | 102599901 A | 7/2012 |

(Continued)

OTHER PUBLICATIONS

Co-pending U.S. Appl. No. 14/997,401, filed Jan. 15, 2016.
(Continued)

*Primary Examiner* — Tammie K Marlen
(74) *Attorney, Agent, or Firm* — Wilson Sonsini Goodrich & Rosati

(57) ABSTRACT

A compact integrated patch may be used to collect physiological data. The patch may be wireless. The patch may be utilized in everyday life as well as in clinical environments. Data acquired by the patch and/or external devices may be interpreted and/or be utilized by healthcare professionals and/or computer algorithms (e.g., third party applications). Data acquired by the patch may be interpreted and be presented for viewing to healthcare professionals and/or ordinary users.

15 Claims, 24 Drawing Sheets

Related U.S. Application Data

(60) Provisional application No. 62/411,254, filed on Oct. 21, 2016, provisional application No. 62/311,808, filed on Mar. 22, 2016.

(51) Int. Cl.
| | |
|---|---|
| *A61B 5/0245* | (2006.01) |
| *G16H 40/67* | (2018.01) |
| *A61N 1/39* | (2006.01) |
| *A61B 5/11* | (2006.01) |
| *A61B 5/1455* | (2006.01) |
| *A61N 1/04* | (2006.01) |
| *A61B 5/01* | (2006.01) |
| *H04L 67/12* | (2022.01) |
| *A61B 5/282* | (2021.01) |
| *A61N 1/36* | (2006.01) |
| *A61N 1/362* | (2006.01) |

(52) U.S. Cl.
CPC ........ *A61B 5/0245* (2013.01); *A61B 5/02433* (2013.01); *A61B 5/1112* (2013.01); *A61B 5/1455* (2013.01); *A61B 5/7207* (2013.01); *A61N 1/0492* (2013.01); *A61N 1/3904* (2017.08); *G16H 40/67* (2018.01); *A61B 5/01* (2013.01); *A61B 5/282* (2021.01); *A61B 2560/0271* (2013.01); *A61B 2560/0412* (2013.01); *A61B 2560/0468* (2013.01); *A61B 2562/0209* (2013.01); *A61B 2562/046* (2013.01); *A61N 1/046* (2013.01); *A61N 1/36014* (2013.01); *A61N 1/3625* (2013.01); *A61N 1/3975* (2013.01); *A61N 1/3987* (2013.01); *H04L 67/12* (2013.01)

(58) Field of Classification Search
CPC ... A61B 5/1112; A61B 5/1455; A61B 5/7207; A61B 5/282; A61B 5/252; A61B 5/259; A61B 5/274; A61B 5/276; A61B 5/01; A61B 2560/0271; A61B 2560/0412; A61B 2560/0468; A61N 1/3904; A61N 1/0492; A61N 1/046; A61N 1/36014; A61N 1/3625; A61N 1/3975; A61N 1/3987; A61N 1/3925; A61N 1/08; A61N 1/3718; G16H 40/67; H04L 67/12

See application file for complete search history.

(56) References Cited

U.S. PATENT DOCUMENTS

| | | |
|---|---|---|
| 3,868,948 A | 3/1975 | Graetz |
| 4,067,342 A | 1/1978 | Burton |
| 4,082,086 A | 4/1978 | Page et al. |
| 4,084,583 A | 4/1978 | Hjort |
| 4,121,573 A | 10/1978 | Crovella et al. |
| 4,365,634 A | 12/1982 | Bare et al. |
| 4,398,545 A | 8/1983 | Wilson |
| 4,624,263 A | 11/1986 | Slavin |
| 4,653,503 A | 3/1987 | Heath |
| 4,705,049 A | 11/1987 | John |
| 5,168,874 A | 12/1992 | Segalowitz |
| 5,372,125 A | 12/1994 | Lyons |
| 5,483,967 A | 1/1996 | Ohtake |
| 5,578,065 A | 11/1996 | Hattori et al. |
| 5,634,468 A | 6/1997 | Platt et al. |
| 5,704,351 A | 1/1998 | Mortara et al. |
| 5,895,369 A | 4/1999 | Flower |
| 5,948,006 A | 9/1999 | Mann |
| 6,104,306 A | 8/2000 | Hogue et al. |
| 6,117,077 A | 9/2000 | Del et al. |
| 6,168,568 B1 | 1/2001 | Gavriely |
| 6,441,747 B1 | 8/2002 | Khair et al. |
| 6,453,186 B1 | 9/2002 | Lovejoy et al. |
| 6,456,720 B1 | 9/2002 | Brimhall et al. |
| 6,814,706 B2 | 11/2004 | Barton et al. |
| 6,897,788 B2 | 5/2005 | Khair et al. |
| 6,965,794 B2 | 11/2005 | Brody |
| 7,156,301 B1 | 1/2007 | Bonalle et al. |
| 7,206,630 B1 | 4/2007 | Tarler et al. |
| 7,257,438 B2 | 8/2007 | Kinast |
| 7,400,298 B2 | 7/2008 | Fogg et al. |
| 7,486,977 B2 | 2/2009 | Sweitzer et al. |
| 7,499,739 B2 | 3/2009 | Sweitzer et al. |
| 7,668,580 B2 | 2/2010 | Shin et al. |
| 7,796,042 B2 | 9/2010 | Walther et al. |
| 7,920,096 B2 | 4/2011 | Fogg et al. |
| 7,969,307 B2 | 6/2011 | Peeters |
| 7,970,450 B2 | 6/2011 | Kroecker et al. |
| 8,150,502 B2 | 4/2012 | Kumar et al. |
| 8,287,386 B2 | 10/2012 | Miller et al. |
| 8,315,687 B2 | 11/2012 | Cross et al. |
| 8,611,980 B2 | 12/2013 | Choe et al. |
| 8,628,020 B2 | 1/2014 | Beck |
| 8,688,189 B2 | 4/2014 | Shennib |
| 8,718,742 B2 | 5/2014 | Beck et al. |
| 8,926,509 B2 | 1/2015 | Magar et al. |
| 9,019,934 B2 | 4/2015 | Yun et al. |
| 9,265,435 B2 | 2/2016 | Beck |
| 9,597,034 B2 | 3/2017 | Beck |
| 2002/0037756 A1 | 3/2002 | Jacobs et al. |
| 2002/0045836 A1 | 4/2002 | Alkawwas |
| 2003/0040305 A1 | 2/2003 | Ng et al. |
| 2003/0069510 A1 | 4/2003 | Semler |
| 2003/0083584 A1 | 5/2003 | Yonce |
| 2004/0019288 A1 | 1/2004 | Kinast |
| 2004/0131897 A1 | 7/2004 | Jenson et al. |
| 2006/0009691 A1 | 1/2006 | Yeo et al. |
| 2006/0030782 A1 | 2/2006 | Shennib et al. |
| 2006/0155183 A1 | 7/2006 | Kroecker et al. |
| 2006/0264767 A1 | 11/2006 | Shennib |
| 2007/0060832 A1 | 3/2007 | Levin |
| 2007/0072443 A1 | 3/2007 | Rohrbach et al. |
| 2007/0093705 A1 | 4/2007 | Shin et al. |
| 2007/0179376 A1 | 8/2007 | Gerder |
| 2007/0293781 A1 | 12/2007 | Sims et al. |
| 2008/0055045 A1 | 3/2008 | Swan et al. |
| 2008/0081960 A1 | 4/2008 | Rantala |
| 2008/0139953 A1 | 6/2008 | Baker et al. |
| 2008/0186241 A1 | 8/2008 | Christensen |
| 2008/0221398 A1 | 9/2008 | Ronchi et al. |
| 2008/0309287 A1 | 12/2008 | Reed |
| 2009/0036792 A1 | 2/2009 | DeLuca et al. |
| 2009/0073991 A1 | 3/2009 | Landrum et al. |
| 2009/0221897 A1 | 9/2009 | Nieuwkoop et al. |
| 2009/0264792 A1* | 10/2009 | Mazar ............ A61B 5/30 600/547 |
| 2009/0292194 A1 | 11/2009 | Libbus et al. |
| 2010/0019721 A1 | 1/2010 | Reggiardo |
| 2010/0049006 A1 | 2/2010 | Magar et al. |
| 2010/0081913 A1 | 4/2010 | Cross et al. |
| 2010/0317958 A1 | 12/2010 | Beck et al. |
| 2010/0326703 A1 | 12/2010 | Gilad et al. |
| 2011/0021937 A1 | 1/2011 | Hugh et al. |
| 2011/0028822 A1 | 2/2011 | Beck |
| 2011/0062241 A1 | 3/2011 | Beck |
| 2011/0065476 A1 | 3/2011 | Hsiao et al. |
| 2011/0270112 A1 | 11/2011 | Manera et al. |
| 2011/0299713 A1 | 12/2011 | Moeller et al. |
| 2012/0029307 A1* | 2/2012 | Paquet ............ A61B 5/0816 600/301 |
| 2012/0088999 A1 | 4/2012 | Bishay et al. |
| 2014/0088398 A1 | 3/2014 | Beck |
| 2014/0228665 A1 | 8/2014 | Albert |
| 2015/0073231 A1 | 3/2015 | Beck et al. |
| 2015/0073252 A1 | 3/2015 | Mazar |
| 2015/0289814 A1 | 10/2015 | Magar et al. |
| 2016/0015962 A1 | 1/2016 | Shokoueinejad et al. |
| 2016/0022161 A1 | 1/2016 | Khair |

(56) References Cited

U.S. PATENT DOCUMENTS

| | | |
|---|---|---|
| 2016/0029906 A1 | 2/2016 | Tompkins et al. |
| 2017/0354376 A1 | 12/2017 | Beck |

FOREIGN PATENT DOCUMENTS

| | | |
|---|---|---|
| CN | 103405228 A | 11/2013 |
| CN | 203841698 U | 9/2014 |
| CN | 105286909 A | 2/2016 |
| WO | WO-0178594 A1 | 10/2001 |
| WO | WO-02089667 A1 | 11/2002 |
| WO | WO-03065926 A2 | 8/2003 |
| WO | WO-03065926 A3 | 6/2004 |
| WO | WO-2005094674 A1 | 10/2005 |
| WO | WO-2006061354 A1 | 6/2006 |
| WO | WO-2007060609 A2 | 5/2007 |
| WO | WO-2007060609 A3 | 10/2007 |
| WO | WO-2008006150 A1 | 1/2008 |
| WO | WO-2015127466 A2 | 11/2015 |
| WO | WO-2017165526 | 9/2017 |

OTHER PUBLICATIONS

International search report and written opinion dated Jan. 7, 2016 for PCT/US2015/042989.
International search report and written opinion dated May 28, 2009 for PCT Application No. US08/80695.
International search report and written opinion dated Jul. 20, 2009 for PCT Application No. US08/80659.
International search report and written opinion dated Sep. 29, 2008 for PCT Application No. US08/64800.
"IPRP for PCT/US2017/023601 Sep. 25, 2018".
Notice of allowance dated Mar. 14, 2014 for U.S. Appl. No. 12/601,373.
Notice of allowance dated Sep. 12, 2013 for U.S. Appl. No. 12/739,561.
Notice of allowance dated Oct. 7, 2015 for U.S. Appl. No. 12/739,553.
Notice of allowance dated Nov. 3, 2015 for U.S. Appl. No. 12/739,553.
Notice of Allowance dated Nov. 23, 2016 for U.S. Appl. No. 14/805,389.
Office action dated Jan. 22, 2015 for U.S. Appl. No. 14/091,252.
Office action dated Feb. 8, 2016 for U.S. Appl. No. 14/805,389.
Office action dated Feb. 27, 2015 for U.S. Appl. No. 14/244,760.
Office action dated Apr. 15, 2013 for U.S. Appl. No. 12/601,373.
Office action dated Jun. 26, 2012 for U.S. Appl. No. 12/739,561.
Office action dated Jul. 30, 2013 for U.S. Appl. No. 12/739,553.
Office Action dated Aug. 3, 2016 for U.S. Appl. No. 14/805,389.
Office action dated Aug. 31, 2012 for U.S. Appl. No. 12/601,373.
Office action dated Oct. 29, 2013 for U.S. Appl. No. 12/601,373.
Office action dated Nov. 21, 2012 for U.S. Appl. No. 12/739,553.
Office action dated Dec. 29, 2014 for U.S. Appl. No. 12/739,553.
EP15827134.6 Extended Search Report dated Feb. 22, 2018.
PCT/US2017/023601 International Search Report dated Jul. 7, 2017.
Wang, Y. et al., A low noise wearable wireless ECG system with body motion cancellation for long term homecare. IEEE 15th international conference on e-health networking, applications and services (healthcom 2013) 507-511.
Co-pending U.S. Appl. No. 17/244,625, inventors Tompkins et al., filed Apr. 29, 2021.
Notice of allowance dated Feb. 4, 2013 for U.S. Appl. No. 12/739,561.
Notice of allowance dated Dec. 19, 2013 for U.S. Appl. No. 12/601,373.
U.S. Appl. No. 14/244,760 Office Action dated Feb. 27, 2015.
U.S. Appl. No. 14/814,436 Notice of Allowance dated Mar. 31, 2021.
U.S. Appl. No. 14/814,436 Office Action dated Feb. 24, 2020.
U.S. Appl. No. 14/814,436 Office Action dated Sep. 1, 2020.
EP17771062.1 Extended European Search Report dated Oct. 29, 2019.
Romanowich, C.A., Voltage used to resuscitate a human heart, The Physics factbook, Jan. 1, 1999, XP055633665.
U.S. Appl. No. 14/814,436 Office Action dated Aug. 27, 2019.
U.S. Appl. No. 14/814,436 Office Action dated Feb. 8, 2019.

\* cited by examiner

SYSTEMS AND METHODS FOR PHYSIOLOGICAL SIGNAL COLLECTION

CROSS-REFERENCE

The present application is a continuation of International Application No. PCT/US2017/023601, filed Mar. 22, 2017, which claims priority to U.S. App. Ser. No. 62/311,808, filed Mar. 22, 2016, and U.S. App. Ser. No. 62/411,254, filed on Oct. 21, 2016, the disclosures of which applications are herein incorporated by reference in their entirety.

BACKGROUND

Monitoring physiological conditions of the human body has been an important component of health care. Increasingly, with sophistication of technology related to sensors and wireless communication, electronics that monitor physiological conditions may become integrated with everyday life and be utilized for purposes of maintaining a healthy lifestyle and/or managing illness.

In some instances, remote health monitoring makes it easier and cost effective to monitor the health of vast populations. Wireless systems may be a desired approach to enable remote health monitoring, and a variety of wireless health monitoring systems have been introduced over the years. Conventional health monitoring systems may be bulky, expensive, have inadequate wireless link reliability, or may have high power dissipation which limits their applications, e.g. to monitoring a wide range of physiological parameters in high volumes for large populations. In some instances, health monitoring systems may inadequately account for concurrent use with other forms of medical equipment such as defibrillators.

SUMMARY

Technologies disclosed herein may overcome drawbacks in the existing physiological monitoring systems. The technologies may miniaturize electrodes and data collection devices. Electrodes may be integrated on a printed circuit board with specially configured resistors to prevent unwanted energy surges. Data collection devices may be designed as portable devices. Wireless interfaces may be integrated on electrodes and data collection devices to facilitate physiological signal collection based on wireless communications technologies. Further, physiological signals may be sent from a data collection device to a server for signal analytics. Analytics results may be sent to a consumer or a patient or a healthcare provider.

In one aspect, disclosed herein is a patch for monitoring physiological data comprising: (a) a base configured to come in contact with a surface of a user; (b) one or more electrodes operably coupled to the base, the one or more electrodes configured to monitor the physiological data from the user; (c) an electronic module in communication with the one or more electrodes, the electronic module configured to receive the monitored physiological data; and (d) one or more resistors operably coupled to the one or more electrodes and/or the electronic module, the one or more resistors configured to protect the patch from an external source of electrical current. The external source of current may be a defibrillation voltage pulse applied to the user. The defibrillation voltage pulse may be applied to the user across the user's chest. The defibrillation voltage pulse may be equal to about or more than 300 V. The external source of current may be a defibrillation voltage pulse applied to the user. The one or more resistors may be configured to protect the one or more electrodes and/or the electronic module of the patch. The one or more resistors may be configured to protect a component of the patch from heat generated by the external source of electrical current. In some instances, a resistance of each of the one or more resistors may be equal to about or more than 100 ohms. The patch may further comprise one or more batteries. In additional design, the one or more resistors may be located about or more than about 1 cm from each of the one or more batteries. The number of the one or more resistors may correspond to at least the number of the one or more electrodes. Each of the one or more electrodes may be operably coupled to a corresponding resistor. The corresponding resistor may be located between each of the one or more electrodes and the electronic module. The electronic module may comprise one or more processors configured to analyze the physiological data. Analyzing the physiological data may infer an ECG signal, or a respiratory signal, or a heart rate, or a combination thereof. The electronic module may comprise a wireless communication means. The wireless communication means may comprise one or more of the following: a near range communication means, a short range communication means, and a long range communication means. The wireless communication means may operate on one or more of the following protocols: a Bluetooth protocol, a Wi-Fi protocol, an ultra-wide band protocol. The patch may be operably coupled to one or more sensors configured to measure additional types of physiological data. The patch may comprise the one or more sensors. Further, the patch may be operably coupled to the one or more sensors via wired or wireless connection. The one or more sensors may comprise a respiration measurement sensor, a SpO2 sensor, or a combination thereof. Each of the one or more sensors may be operably coupled to a corresponding resistor. In various implementations, the patch may comprise at least four electrodes comprising at least a right arm (RA), left arm (LA), right leg (RL), and left leg (LL) electrode, and the corresponding resistor is also operably coupled to the RA and/or LL electrode. The patch may comprise four or more electrodes configured to gather information sufficient to generate at least three limb leads. The patch may be equal to or less than about 1 inch thick. The four electrodes may comprise at least a right arm (RA), left arm (LA), right leg (RL), and left leg (LL) electrode. The patches may comprise two or more batteries. The two or more batteries may be located between the RA and RL electrodes, and between the LA and LL electrodes. The one or more electrodes, the electronic module, and the one or more resistors may be located on a single layer. The single layer may further comprise one or more batteries.

In another aspect, disclosed herein is a method for protecting a patch from an external source of electrical current comprising: (a) contacting a surface of a user with a base of the patch, wherein the patch comprises: (1) one or more electrodes operably coupled to the base, the one or more electrodes configured to monitor physiological data from the user; (2) an electronic module in communication with the one or more electrodes, the electronic module configured to receive the monitored physiological data; and (3) one or more resistors operably coupled to the one or more electrodes and/or the electronic module; (b) receiving an external source of electrical current at the patch; and (c) protecting the patch from the external source of electrical current with aid of the one or more resistors. The external source of current may be a defibrillation voltage pulse applied to the user. The defibrillation voltage pulse may be applied to the user across the user's chest. The defibrillation voltage pulse may be equal to about or more than 300 V. The external source of current may be a defibrillation voltage pulse applied to the user. The one or more resistors may be configured to protect the one or more electrodes and/or the electronic module of the patch. The one or more resistors may be configured to protect a component of the patch from heat generated by the external source of electrical current. A resistance of each of the one or more resistors may be equal to about or more than 100 ohms. The patch further comprises one or more batteries. The one or more resistors may be located about or more than about 1 cm from each of the one or more batteries. The number of the one or more resistors may correspond to at least the number of the one or more electrodes. Each of the one or more electrodes may be operably coupled to a corresponding resistor. The corresponding resistor may be located between each of the one or more electrodes and the electronic module. The electronic module may comprise one or more processors configured to analyze the physiological data. Analyzing the physiological data infers an ECG signal, or a respiratory signal, or a heart rate, or a combination thereof. The electronic module may comprise a wireless communication means. The wireless communication means may comprise one or more of the following: a near range communication means, a short range communication means, and a long range communication means. The wireless communication means may operate on one or more of the following protocols: a Bluetooth protocol, a Wi-Fi protocol, a medical hand, and an ultra-wide hand protocol. The patch may be operably coupled to one or more sensors configured to measure additional types of physiological data. The patch may comprise the one or more sensors. The patch may be operably coupled to the one or more sensors via wired or wireless connection. The one or more sensors may comprise a respiration measurement sensor, or a SpO2 sensor, or a combination thereof. Each of the one or more sensors may be operably coupled to a corresponding resistor. The patch may comprise at least four electrodes comprising at least a right arm (RA), left arm (LA), right leg (RL), and left leg (LL) electrode, and the corresponding resistor is also operably coupled to the RA and/or LL electrode. The patch may comprise four or more electrodes configured to gather information sufficient to generate at least three limb leads. The patch may be equal to or less than about 1 inch thick. The four electrodes may comprise at least a right arm (RA), left arm (LA), right leg (RL), and left leg (LL) electrode. The patches may comprise one, two, or more batteries. The one, two or more batteries may be located between the RA and RL electrodes, and/or between the LA and LL electrodes. The one or more electrodes, the electronic module, and the one or more resistors may be located on a single layer. The single layer may further comprise one or more batteries.

In another aspect, disclosed herein is a patch for monitoring physiological data comprising: (a) a base configured to come in contact with a surface of a user; (b) one or more electrodes operably coupled to the base, the one or more electrodes configured to monitor the physiological data from the user; and (c) an electronic module in communication with the one or more electrodes, the electronic module being configured to receive the monitored physiological data, wherein the patch may be configured to wirelessly communicate with two or more different types of devices. The two or more different types of devices may comprise at least two of a mobile device, a data collection device, and a patient monitor. The patch may be configured to communicate with the data collection device via Wi-Fi, MBand, and/or UWB. The patch may be configured to communicate with the mobile device via Wi-Fi. The patch may be configured to communicate with the patient monitor via Wi-Fi, MBand, and/or UWB. The patch may be configured to communicate with the patient monitor with aid of an adapter. The data collection device may be further configured to communicate with the mobile device and/or the patient monitor. The patient monitor and/or mobile device may be further configured to communicate with an external server. A type of device that the patch communicates with may be selected by the user. A type of device the patch communicates with may be selected by a healthcare professional. The patch may be configured to communicate with the two or more devices using different communication schemes. The patch may be configured to communicate with the two or more devices using a same communication scheme. The patch may be configured to communicate with the two or more devices as an alternative. The patch may be configured to communicate with three or more different types of devices. The three or more different types of devices may comprise a mobile device, a data collection device, and a patient monitor.

In another aspect, disclosed herein is a method for monitoring physiological data, the method comprising: (a) contacting a surface of a user with a base of the patch, wherein the patch comprises: monitoring, with aid of one or more electrodes operably coupled to the base, the physiological data from the user; and receiving, at an electronic module in communication with the one or more electrodes, the monitored physiological data; and (b) wirelessly transmitting the received physiological data to two or more different types of devices. The two or more different types of devices may comprise at least two of a mobile device, a data collection device, and a patient monitor. The patch may be configured to communicate with the data collection device via Wi-Fi, MBand, and/or UWB. The patch may be configured to communicate with the mobile device via Wi-Fi. The patch may be configured to communicate with the patient monitor via Wi-Fi, MBand, and/or UWB. The patch may be configured to communicate with the patient monitor with aid of an adapter. The data collection device may be further configured to communicate with the mobile device and/or the patient monitor. The patient monitor and/or mobile device may be further configured to communicate with an external server. A type of device the patch communicates with may be selected by the user. A type of device the patch communicates with may be selected by a healthcare professional. The patch may be configured to communicate with the two or more devices using different communication schemes. The patch may be configured to communicate with the two or more devices using a same communication scheme. The patch may be configured to communicate with the two or more devices as an alternative. The patch may be configured to communicate with three or more different types of devices. The three or more different types of devices may comprise a mobile device, a data collection device, and a patient monitor.

In another aspect, disclosed herein is a system for monitoring physiological data, the system comprising: (a) a patch configured to monitor the physiological data from a user; (b) a data collection device in wireless communication with the patch, the data collection device configured to receive the monitored physiological data from the patch, wherein the data collection device weighs less than or equal to 2 grams. The data collection device may comprise a maximum dimension equal to or smaller than 8 cm. The data collection device may comprise a volume equal to or smaller than 30 $cm^3$. The data collection device may be in a form of a card. The data collection device may be in a form of a wrist band.

The data collection device may comprise a memory. The data collection device may be capable of storing physiological data measured from the user for at least two days or more. The data collection device may be configured for Holter monitoring, event monitoring, and/or loop monitoring. The data collection device may be configured to store and/or transmit the received physiological data to another device or a server in real time. The data collection device may be configured to transmit the received physiological data to another device or a server after data collection is completed. The data collection device may be configured to transmit the received physiological data to another device or a server in batch file. The data collection device may be not configured to analyze the received physiological data. The data collection device may be configured track a location of the user. The data collection device may comprise a GPS. The data collection device may comprise a user interface. The user interface may comprise one or more buttons. Actuation of the one or more buttons may signal a beginning of an event for event monitoring. Actuation of the one or more buttons may be configured to record and store a message from the user in the data collection device with aid of a microphone. The user interface may comprise a touchscreen display. The data collection device may comprise a microphone. The data collection device may be configured to communicate with a mobile device. The mobile device may be a cellphone, a pda, and/or a tablet. The data collection device may be configured to communicate with a patient monitor. The data collection device may be configured to communicate with the patient monitor with aid of an adapter. The data collection device may be further configured to communicate with two or more different types of devices. The two or more different types of devices may comprise a patient monitor and a mobile device. The system may further comprise a server configured to receive the physiological data, wherein the server may be configured to perform analytics on the physiological data. The data collection device may communicate with the patch via Wi-Fi, MBand, and/or UWB. The patch may be further configured to communicate with a third device. The patch may be configured to communicate with the third device via the data collection device. The data collection device may extend a communication distance for the patch to communicate with the third device. The data collection device may extend the communication distance between the patch and the third device by at least 2 times as compared to not having the data collection device.

In another aspect, disclosed herein is a method for monitoring physiological data, the method comprising: (a) monitoring the physiological data from a user; and (h) receiving the monitored physiological data from the patch, wherein the data collection device weights less than or equal to 2 grams. The data collection device may comprise a maximum dimension equal to or smaller than 8 cm. The data collection device may comprise a volume equal to or smaller than 30 cm$^3$. The data collection device may be in a form of a card. The data collection device may be in a form of a wrist band. The data collection device may comprise a memory. The data collection device may be capable of storing physiological data measured from the user for at least two days or more. The data collection device may be configured for Holter monitoring, event monitoring, and/or loop monitoring. The data collection device may be configured to store and/or transmit the received physiological data to another device or a server in real time. The data collection device may be configured to transmit the received physiological data to another device or a server after data collection is completed. The data collection device may be configured to transmit the received physiological data to another device or a server in batch file. The data collection device may be not configured to analyze the received physiological data. The data collection device may be configured track a location of the user. The data collection device may comprise a GPS. The data collection device may comprise a user interface. The user interface may comprise one or more buttons. Actuation of the one or more buttons may signal a beginning of an event for event monitoring. Actuation of the one or more buttons may be configured to record and store a message from the user in the data collection device with aid of a microphone. The user interface may comprise a touchscreen display. The data collection device may comprise a microphone. The data collection device may be configured to communicate with a mobile device. The mobile device may be a cellphone, a pda, and/or a tablet. The data collection device may be configured to communicate with a patient monitor. The data collection device may be configured to communicate with the patient monitor with aid of an adapter. The data collection device may be further configured to communicate with two or more different types of devices. The two or more different types of devices may comprise a patient monitor and a mobile device. The system may further comprise a server configured to receive the physiological data, wherein the server may be configured to perform analytics on the physiological data. The data collection device may communicate with the patch via Wi-Fi, MBand, and/or UWB. The patch may be further configured to communicate with a third device. The patch may be configured to communicate with the third device via the data collection device. The data collection device may extend a communication distance for the patch to communicate with the third device. The data collection device may extend the communication distance between the patch and the third device by at least 2 times as compared to not having the data collection device.

It shall be understood that different aspects of the present disclosure can be appreciated individually, collectively, or in combination with each other. Various aspects of the disclosure described herein may be applied to any of the particular applications set forth below. Other objects and features of the present disclosure will become apparent by a review of the specification, claims, and appended figures.

INCORPORATION BY REFERENCE

All publications, patents, and patent applications mentioned in this specification are herein incorporated by reference to the same extent as if each individual publication, patent, or patent application was specifically and individually indicated to be incorporated by reference in their entirety.

BRIEF DESCRIPTION OF THE DRAWINGS

The technical features of the present disclosure are set forth with particularity in the appended claims. A better understanding of the features and advantages of the present disclosure will be obtained by reference to the following detailed description that sets forth illustrative embodiments, in which the principles of the disclosure are utilized, and the accompanying drawings of the following.

DETAILED DESCRIPTION

While various embodiments are shown and described herein, it will be obvious to those skilled in the art that such embodiments are provided by way of example only. Numerous variations, changes, and substitutions may occur to those skilled in the art without departing from devices, systems and methods disclosed herein. It should be understood that various alternatives to the embodiments described herein may be employed.

Unless otherwise defined, all technical terms used herein have the same meaning as commonly understood by one of ordinary skill in the art to which this disclosure belongs. As used in this specification and the appended claims, the singular forms "a," "an," and "the" include plural references unless the context clearly dictates otherwise. Any reference to "or" herein is intended to encompass "and/or" unless otherwise stated.

The present disclosure provides technologies that may miniaturize electrodes and data collection devices and/or make their use more convenient. Wireless communications technologies may be employed to link electrodes and data collection devices. Further, physiological signals collected by the data collection devices may be sent to a server for signal analytics. Results from the analysis may be delivered to various parties, such as a healthcare provider, a patient, or a family member. In some instances, the systems and methods disclosed herein may help simplify a health monitoring process and/or may help create an agile, portable health monitoring systems. In some instances, the systems and methods disclosed herein may enable widespread or ubiquitous health monitoring based on portable devices.

Technologies Overview

The technologies disclosed herein may support various health monitoring procedures. Examples of the health monitoring procedures include, but are not limited to: multi-day live monitoring where a user may be monitored by a remote healthcare provider or a family member; in-patient monitoring where data is continuously displayed on patient monitors to facilitate patient monitoring; ambulatory outpatient monitoring where an ambulatory staff member can monitor physiological signals and correlate the physiological signals with symptoms; Holter monitoring where a person's various electrical activity of cardiovascular system can last more than 24 hours; event monitoring where an event can be flagged either by a patient or others, e.g. by pressing a button and few minutes of data may be transmitted on occurrence of an event.

Figure 1:
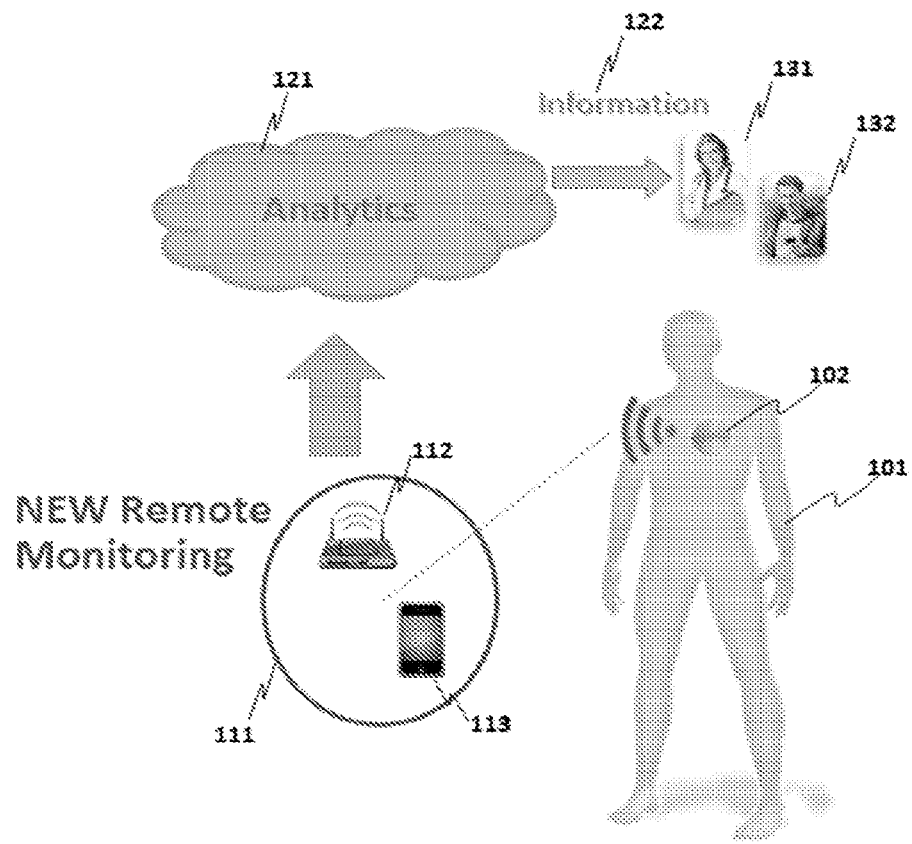
FIG. 1 illustrates an exemplary health monitoring system.

FIG. 1 illustrates an exemplary health monitoring system. To monitor a user 101, a patch 102 with capabilities of sensing and wireless communication may be attached to the user 101. A user may be a patient with a disease state (e.g., cardiac abnormality), or a person willing to know his/her health condition. The physiological signals of a user may be transmitted to one or more wireless devices 111. Upon receiving the physiological signals, the wireless devices 111 may further transmit the signals to a server 121 for signal analysis. In various embodiments, a signal may be transmitted from an electrode patch 102 directly to a server 121, or via a wireless device 111 to a server 121. The extracted information 122 may further be transmitted to a health care provider 131 and/or a patient 132 and/or a family member.

In various embodiments, a patch 102 may be placed on a forehead or on a chest to measure physiological signals (e.g., electrocardiogram (ECG) and photoplethysmographic signals. A patch 102 may collect signals for at least one cardiac cycle, or at least 5 minutes, or at least one hour, or at least 24 hours, or at least 3 days in a row. Examples of wireless devices 111 include a Wi-Fi access point 112 or a mobile device 113, which may relay signals from patch 102 to analytics server.

Patch

Figure 2A:
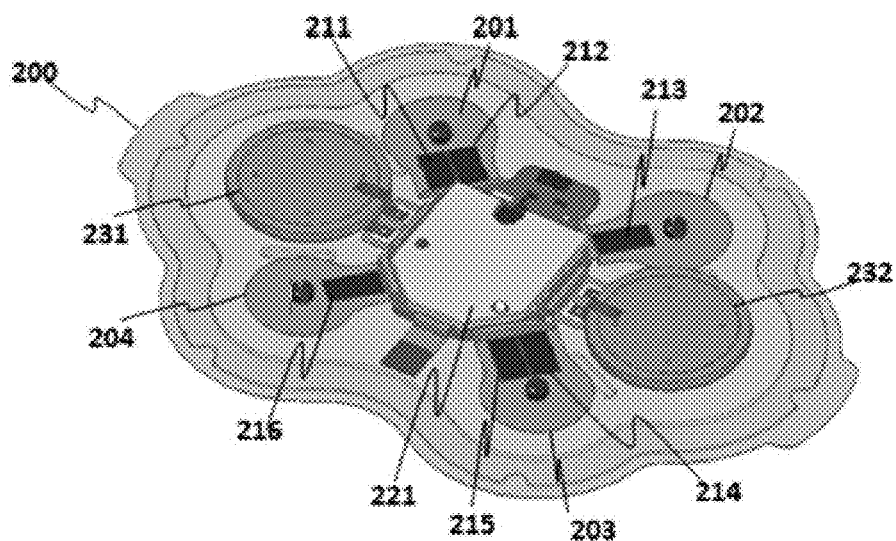
FIG. 2A illustrates a schematic design of a patch.
Figure 2B:
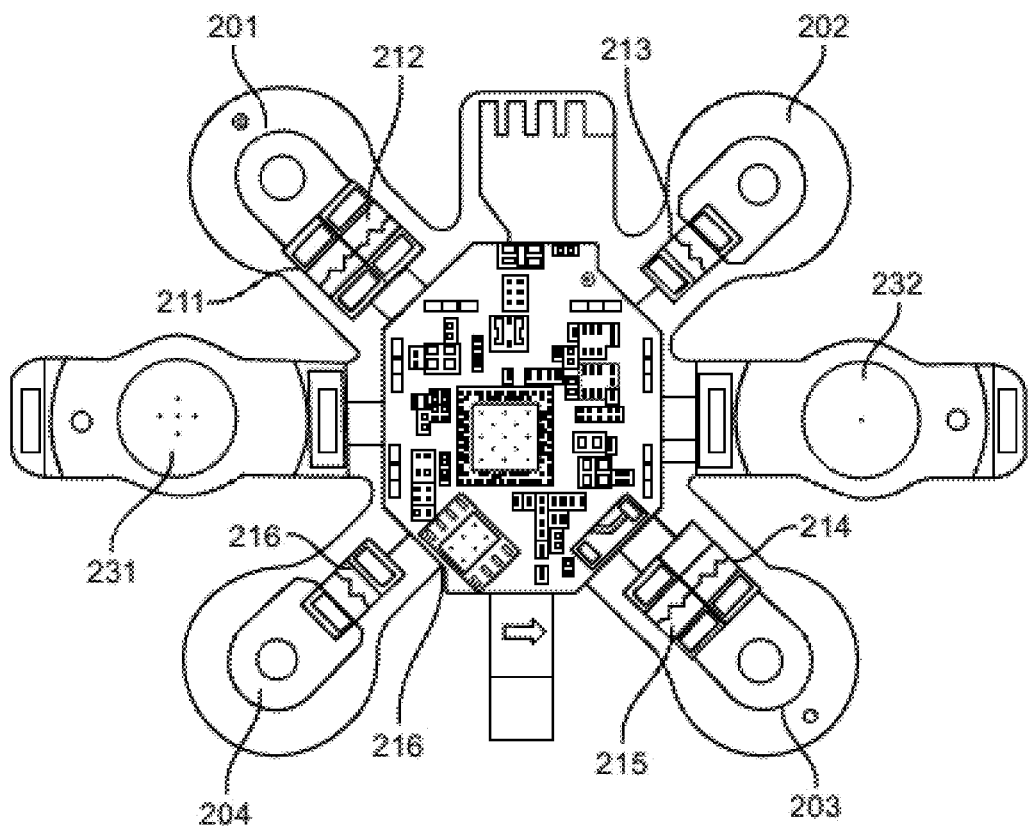
FIG. 2B shows an example of a patch.

A system disclosed herein may comprise a patch, or use of the same. FIG. 2A illustrates a schematic patch, and FIG. 2B shows an example embodiment of a patch. A patch may be designed for monitoring physiological data. Examples of physiological data include, but not limited to, heart rate, body temperature, conductivity, impedance, resistance, synaptic signals, neural signals, voice signals, vision or optical signals, electrocardiography, electroatriography, electroventriculography, intracardiac electrogram, electroencephalography, electrocorticography, electromyography, electrooculography, electroretinography, electronystagmography, electroolfactography, electroantennography, electrocochleography, electrogastrography, electrogastroenterography, electroglottography, electropalatography, electroarteriography, electroblepharography, electrodennography, electrohysterography, electroneuronography, electropneumography, electrospinography, and electrovomerography.

A patch may comprise a base 200. A base 200 may comprise a flexible substrate. Materials of a base 200 may comprise a plastic material or a silicone material. One surface of a base may be used for holding electrodes and/or electronic components. Another surface of the base may be designed to contact with a user at a forehead, an arm, a chest, a leg, and a finger. A patch may comprise one or more electrodes. The number of electrodes may be 2, 3, 4, 5, 6, 7, 8, 9, 10, 11, 12, 13, 14, 15, 16, 17, 18, 19, 20 or more than 20. In an example illustrated in FIGS. 2A and 2B, four electrodes (201, 202, 203, and 204) may be operably coupled to the base 200, the one or more electrodes configured to monitor the physiological data from the user.

A patch may comprise an electronic module 221 in communication with the one or more electrodes. The electronic module may be configured to receive the monitored physiological data. The electronic module may comprise one or more of the following: a processor, a memory unit, a data storage medium, and one or more wireless communication interfaces. The patch may comprise one or more resistors (211, 212, 213, 214, 215, and 216) operably coupled to the one or more electrodes and/or the electronic module, the one or more resistors configured to protect the patch from an external source of electrical current.

In some implementations, the patch may comprise one or more resistors. A resistor may be operably coupled to an electrode to prevent the electrode and/or an electronic module from an electrical surge. In FIGS. 2A and 2B, six resistors (211, 212, 213, 214, 215, and 216) may be operably coupled to the one or more electrodes and/or the electronic module 221. The patch may receive an external source of electrical energy, current or voltage. The one or more resistors in a patch may protect the patch from the external source of electrical energy, current or voltage. Such external source may comprise abrupt electricity outage, sudden powering on, a medical procedure, or a defibrillation. For example, a patient with cardiac abnormality may need a defibrillation process, and a defibrillation voltage pulse may be applied to the user's chest; without protection by the resistors, one or more electrodes and/or an electronic component may be damaged. In another example, a machine may be suddenly powered on to induce a surge electric current, and a resistor may be used to prevent internal circuitry from the surge that interferes the true physiological signals. A voltage surge (e.g., a defibrillation pulse) may be greater than or equal to about 12 volts (V), 50 V, 75V, 100V, 125V, 150V, 170V, 200V, 225V, 250V, 275V, 300V, 350V, 400V, 500V, 600V, 800V, 1000V, 1200V, 1500V, 2000V, 2500V, 3000V, 4000V, 5000V, or more.

A resistance of each of the one or more resistors may be greater than or equal to about 100, 200, 300, 400, 500, 600, 700, 800, 900, 1 k, 2 k, 3 k, 4 k, 5 k, 6 k, 7 k, 8 k, 9 k, 10 k, 20 k, 30 k, 40 k, 50 k, 60 k, 70 k, 80 k, 90 k, 100 k, 200 k, 300 k, 400 k, 500 k, 600 k, 700 k, 800 k, 900 k, or 1M ohms.

In various implementations, a patch may comprise one or more batteries 231 and 232. One or more resistors may be separated by a distance equal to, or more than about 1 cm from each of the one or more batteries. Such separation may in some instances be less than or equal to about 0.1 cm, 0.2 cm, 0.3 cm, 0.4 cm, 0.5 cm, 0.6 cm, 0.7 cm, 0.8 cm, 0.9 cm, 1 cm, 2 cm, 3 cm, 4 cm, 5 cm, 6 cm, 7 cm, 8 cm, 9 cm, or 10 cm. In some instances, the one or more resistors may be separated from each of the one or more batteries by a distance sufficient to avoid electrostatic discharge. Optionally, a minimum distance required to handle a 5000V surge voltage may be equal to 0.4 cm.

In some instances a number of one or more resistors (211, 212, 213, 214, 215, and 216) may correspond to at least a number of the one or more electrodes (201, 202, 203, and 204). Each of the one or more electrodes may be operably coupled to a corresponding resistor. The one or more resistors coupled to the one or more electrodes may protect the electrode. When each electrode is coupled with one or more resistors, all the electrodes may be protected. In some instances, resistors may protect any electric or electronic components connected with the electrodes. In some instances, e.g. as illustrated in FIGS. 2A and 2B, a corresponding resistor may be located between each of the one or more electrodes and the electronic module. The configuration may allow the resistor to absorb electrical surges impacting the electronic module.

Referring again to FIGS. 2A and 2B, an electronic module 221 in a patch may comprise one or more processors configured to analyze physiological data. Analyzing the physiological data may infer an ECG signal, a respiratory signal, a heart rate, or a combination thereof.

Referring again to FIGS. 2A and 2B, an electronic module 221 may comprise a wireless communication unit. A wireless communication unit may comprise one or more of the following: a near range communication means, a short range communication means, and a long range communication means. A wireless communication unit may operate on one or more of the following protocols: a Bluetooth protocol, a Wi-Fi protocol, an ultra-wide band protocol. Optionally, the electronic module may comprise one or more of the following: instrumentation amplifiers for ECG and/or respiration signals, signal generation units for impedance variation measurement, right leg driver circuits, antennae, transimpedance amplifiers with LED driver circuits for SpO2. In some instances, the electronic module may comprise microprocessors, FLASH memory, LED indicators, voltage and temperature sensors, power management units and defibrillation (or voltage surge) protection circuits with resistors and clamping diodes.

A patch may be operably coupled to one or more sensors configured to measure additional types of physiological data. In some instances, a patch may comprise the one or more sensors. In some designs, a sensor may be integrated on a printed circuit board, where the printed circuit board is hold by the base 200. In some embodiments, a sensor may be directly coupled to an electronic module on a patch. A patch may be operably coupled to the one or more sensors via wired or wireless connection. A patch may comprise a wireless communication interface, and the signals sensed by a sensor are transmitted out via the wireless interface. Alternatively, a patch may comprise a wired communication interface, and the signals sensed by a sensor are transmitted out via the wired interface. The one or more sensors may comprise a respiration measurement sensor, a SpO2 sensor, or both. Each of the one or more sensors may be operably coupled to a resistor, wherein the resistor is designed to prevent electrical surge from the one or more sensors.

Referring again to FIGS. 2A and 2B, in some embodiments, a patch comprises at least four electrodes comprising at least a right arm (RA, 201), left arm (LA, 202), right leg (RL, 204), and left leg (LL, 203) electrodes. These electrodes are coupled with individual resistors 211, 213, 216, and 214. Further, resistors 212 and 215 are also operably coupled to the RA and LL electrodes, respectively. The resistors 212 and 215 may protect respiration measurement circuitry.

A patch may comprise four or more electrodes configured to gather information sufficient to generate at least three limb leads. The electrodes may comprise at least a right arm (RA), left arm (LA), right leg (RL), and left leg (LL) electrode. The patches may comprise two or more batteries. The two or more batteries may be located between the RA and RL electrodes, and between the LA and LL electrodes.

Figure 3:
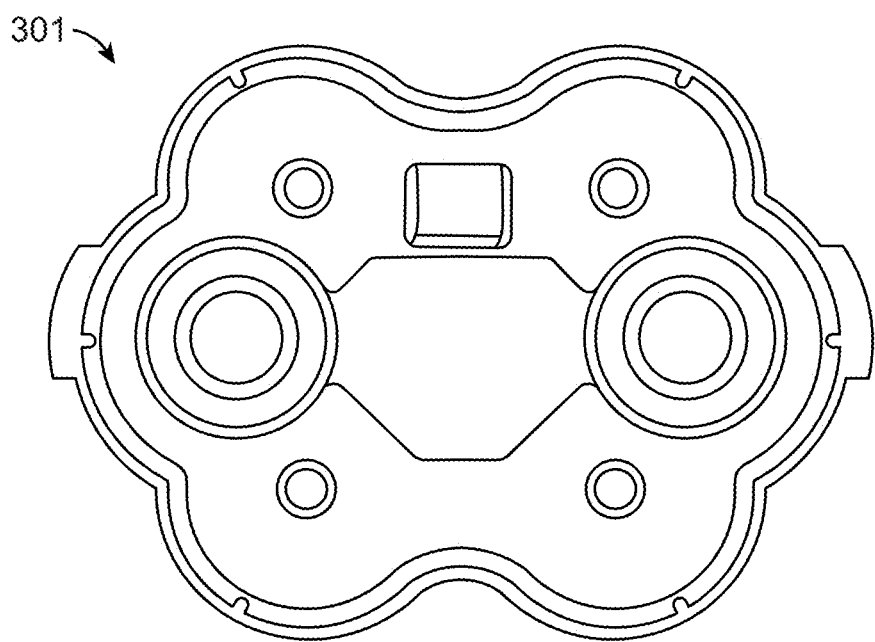
FIG. 3 shows an example of an exterior of a patch.
Figure 3:
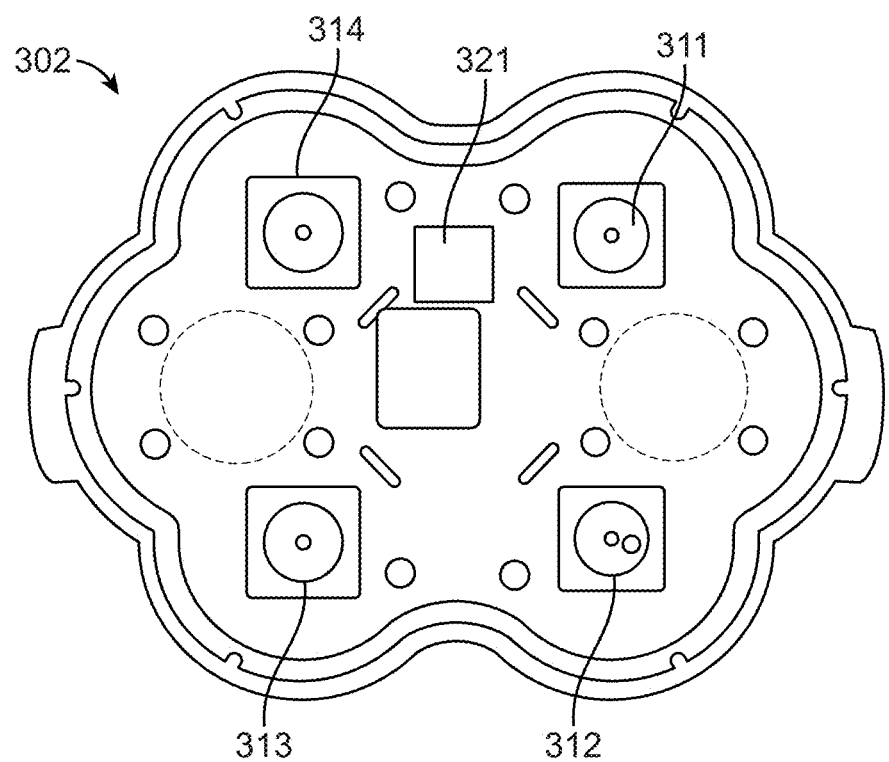

FIG. 3 shows an embodiment of a patch. In this example, the patch is encapsulated by a top layer and a bottom layer. The thickness of a patch may be equal or less than 0.1 inches, 0.2 inches, 0.3 inches, 0.4 inches, 0.5 inches, 0.6 inches, 0.7 inches, 0.8 inches, 0.9 inches, 1 inch, 2 inches, 3 inches, 4 inches, or 5 inches. The weight of a patch may be equal or less than 10 grams, 20 grams, 30 grams, 40 grams, 50 grams, 60 grams 70 grams, 80 grams, 90 grams, 100 grams, 200 grams, 300 grams, 400 grams, or 500 grams. Electrodes and resistors are on a single layer being sandwiched by a top layer and a bottom layer. A top layer of the patch is shown in 301. A bottom layer of the patch is shown in 302. Further, the bottom layer may comprise four electrode contacts 311, 312, 313, and 314. In addition, the bottom layer may comprise a sticker 321. To collect a physiological signal, the bottom layer is attached to a patient's skin. The thin, light patch may provide various benefits. One benefit may be to allow a user to easily carry the patch. Another exemplary benefit may be to allow a user to use the patch on a daily basis. Another benefit is low energy consumption. Another benefit may be to allow easy configuration, or handling of the patch. Another benefit may be to provide a patch without need to worry about wiring as the patch may comprises a wireless communication capability.

The one or more electrodes, the electronic module, and the one or more resistors may be located on a single layer. The single layer can further comprise one or more batteries.

In some examples, a patch for monitoring physiological data may comprise an electronic module in communication with one or more electrodes. The electronic module may be configured to receive the monitored physiological data. In some instances, a patch may be configured to communicate with two or more different types of devices. The two or more different types of devices comprise at least two of a mobile device, a data collection device, and a patient monitor. A patch may be configured to communicate with the data collection device via Wi-Fi, MBand, and/or UWB. A patch may be configured to communicate with the mobile device via Wi-Fi. A patch may be configured to communicate with the patient monitor via Wi-Fi, MBand, and/or UWB. A patch may be configured to communicate with the patient monitor with aid of an adapter. A data collection device may be further configured to communicate with the mobile device and/or the patient monitor.

A patient monitor and/or mobile device may be further configured to communicate with an external server. A type of device the patch communicates with may be selected by the user. A type of device the patch communicates with may be selected by a healthcare professional. A patch may be configured to communicate with the two or more devices using different communication schemes. A patch may be configured to communicate with the two or more devices using a same communication scheme. A patch may be configured to communicate with the two or more devices as an alternative. A patch may be configured to communicate with three or more different types of devices. In some cases, three or more different types of devices comprise a mobile device, a data collection device, and a patient monitor.

Figure 4:
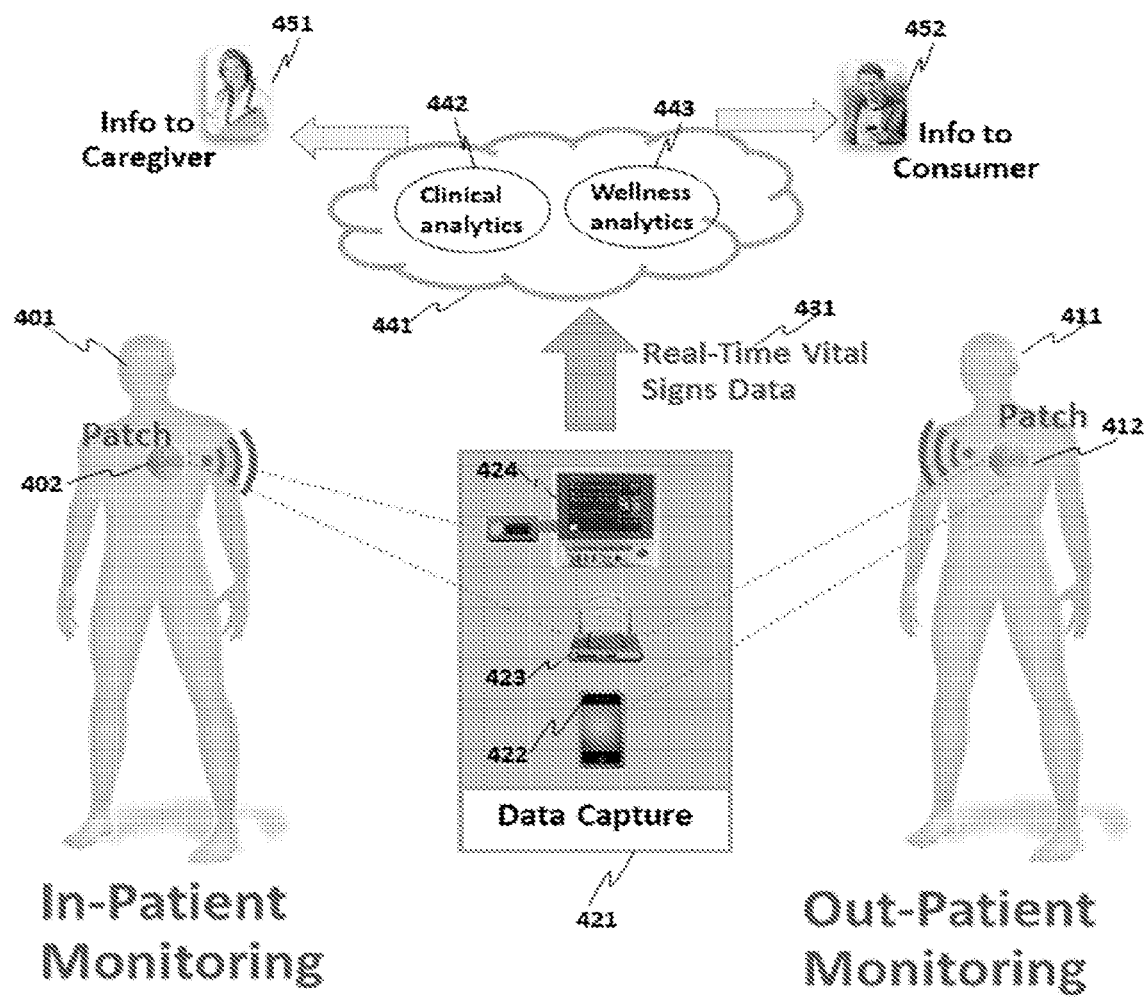
FIG. 4 illustrates an embodiment of a health monitoring system.

FIG. 4 illustrates an embodiment of a system architecture, where a patch may be able to communicate with two devices. A user 401 may be under an in-patient monitoring system. A patch 402 may be attached to the patient 401. The patch 402 may be configured to communicate with at least one component of a data capture system 421. In this case, the patch 402 may be configured to communicate with and a wireless access point 423 and patient monitor 424. On the other hand, a user 411 may be under an out-patient monitoring system. A patch 412 may be attached to the user 411. The patch 412 may be configured to communicate with at least one component of a data capture system 421. In this example, the patch 412 may be configured to communicate with a wireless access point 423 and a mobile device 422. The collected physiological signals 431 by the data capture system 421 may be transmitted to a remote server 441. The server 441 may comprises a computer program including a clinical analytics unit 442 and a wellness analytics unit 443. The analyzed results by a clinical analytics unit 442 may be sent to a health care provider 451. The results of analyses by a wellness analytics unit 443 may be sent to a consumer 452. A consumer 452 may be a patient 411, or another family member of the patient 411, or a person authorized by the patient 411 an access to the wellness analysis results.

SpO2 Sensors

A patch disclosed herein may comprise a SpO2 sensor. A SpO2 sensor may be integrated on a patch. The SpO2 sensor may comprise a light or radiation emitter that outputs a multi-frequency light to the patient at forehead, fingers and/or chest. The SpO2 sensor may comprise a detector to sense the light passing through, or reflecting from, the patient for obtaining data from the patient. The SpO2 sensor may further calculate the oxygen saturation level of blood (SpO2) from the acquired data. In some examples, other components for the pulse oximeter may be also mounted to the patch.

A patch may include an oximetry circuitry, an optional display, an optional alarm possibly in the form of a piezoelectric transducer (audible) and/or an optical indicator on the display (visual) and the power source.

A power source may comprise a thin conventional button battery, or a fuel cell battery, that may also be embedded in the same layer as an electronics chip.

Arterial oxygen saturation may be defined as $$S_aO_2 = \frac{C_{HbO_2}}{C_{total\_hemoglobin}} \times 100\%.$$

Peripheral capillary oxygen saturation measured using a two wavelength pulse oximeters may be defined as $$S_PO_2 = \frac{C_{HbO_2}}{C_{HbO2} + C_{Hb}} \times 100\%$$

The basic equation for measuring SpO2 may be based on Beer-Lambert model, which describes attenuation of light with respect to material through which it is travelling. The intensity of light transmitted through the solution may be $$I = I_0 \exp\left(\sum_i -\varepsilon_i(\lambda)c_i d\right)$$

where $I_0$ is transmitted light, d is optical path length, $\varepsilon_i(\lambda)$ is wavelength dependent extinction coefficient, and $c_i$ is concentration of the i-th absorber. For a solution containing N components, if the extinction coefficients are known and N different wavelengths are considered, the equation can be solved for concentration of N components.

Figure 6:
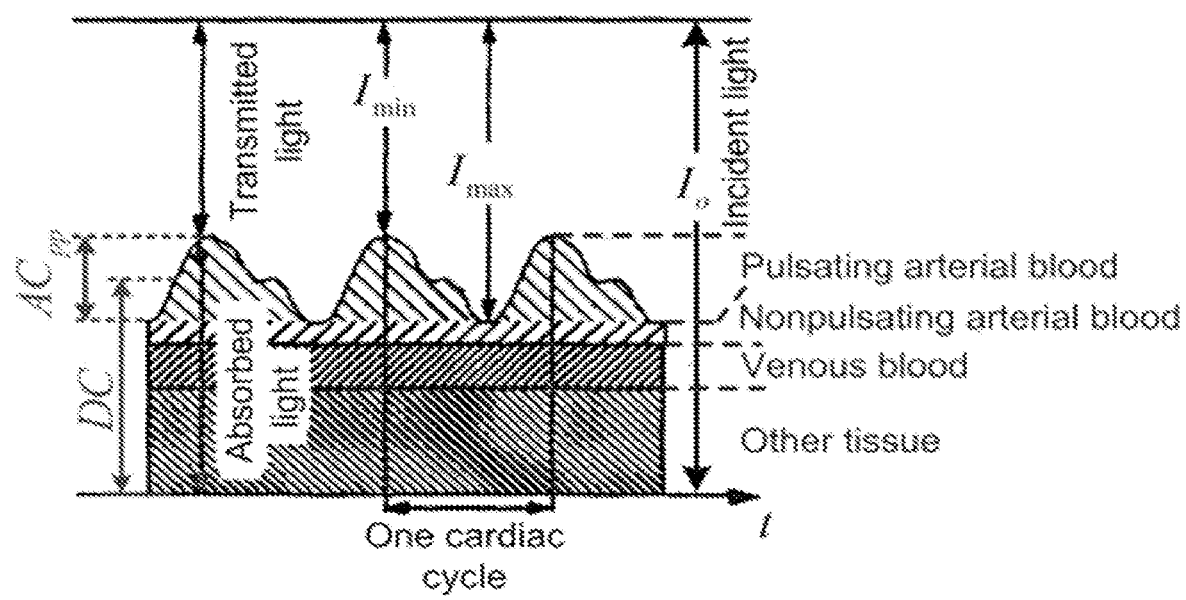
FIG. 6 illustrates light intensity variations measured when light is applied on tissue.

Referring to FIG. 6, when light is applied on tissue, the light may be absorbed by tissue, bone, arterial blood, and/or venous blood. Time varying component such as pulsatile/AC component may be effectively modelled as variation in optical path d and d+Δd. An average value may be a nonpulsatile or DC component.

A ratio of the light measured at peak (diastole) and valley (systole) may be $$\frac{I_{max}}{I_{min}}\bigg|_{\lambda_1} = \frac{I_0 \exp(-[\varepsilon_{HbO2}(\lambda_1)c_{HbO2} + \varepsilon_{Hb}(\lambda_1)c_{Hb}]d)}{I_0 \exp(-[\varepsilon_{HbO2}(\lambda_1)c_{HbO2} + \varepsilon_{Hb}(\lambda_1)c_{Hb}]d + \Delta d)} =$$
$$\exp([\varepsilon_{HbO2}(\lambda_1)c_{HbO2} + \varepsilon_{Hb}(\lambda_1)c_{Hb}]\Delta d)$$

Taking logarithm, $$\ln\left(\frac{I_{max}}{I_{min}}\bigg|_{\lambda_1}\right) = \ln\left(\frac{I_{dc} + I_{ac}/2}{I_{dc} - I_{ac}/2}\bigg|_{\lambda_1}\right) = \ln\left(\frac{1 + \frac{I_{ac}/2}{I_{dc}}}{1 - \frac{I_{ac}/2}{I_{dc}}}\bigg|_{\lambda_1}\right) \approx \frac{I_{ac}}{I_{dc}}\bigg|_{\lambda_1}$$

The ratio becomes $$R_{\lambda_1} = \frac{I_{ac}}{I_{dc}}\bigg|_{\lambda_1} = [\varepsilon_{HbO2}(\lambda_1)c_{HbO2} + \varepsilon_{Hb}(\lambda_1)c_{Hb}]\Delta d$$

To eliminate the unknown distance Δd, the ratio may be found for another wavelength ($\lambda_2$) and then ratio of ratios is computed $$R = \frac{\frac{I_{ac}}{I_{dc}}\big|_{\lambda_1}}{\frac{I_{ac}}{I_{dc}}\big|_{\lambda_2}}$$
$$= \frac{[\varepsilon_{HbO2}(\lambda_1)c_{HbO2} + \varepsilon_{Hb}(\lambda_1)c_{Hb}]\Delta d}{[\varepsilon_{HbO2}(\lambda_2)c_{HbO2} + \varepsilon_{Hb}(\lambda_2)c_{Hb}]\Delta d}$$
$$= \frac{\varepsilon_{HbO2}(\lambda_1)c_{HbO2} + \varepsilon_{Hb}(\lambda_1)c_{Hb}}{\varepsilon_{HbO2}(\lambda_2)c_{HbO2} + \varepsilon_{Hb}(\lambda_2)c_{Hb}}$$

Substituting for SpO2, $$R = \frac{\varepsilon_{HbO2}(\lambda_1)SpO2 + \varepsilon_{Hb}(\lambda_1)(1 - SpO2)}{\varepsilon_{HbO2}(\lambda_2)SpO2 + \varepsilon_{Hb}(\lambda_2)(1 - SpO2)}$$

Then, the solution becomes $$SpO2 = \frac{\varepsilon_{Hb}(\lambda_1) - \varepsilon_{Hb}(\lambda_2)R}{\varepsilon_{Hb}(\lambda_1) - \varepsilon_{HbO2}(\lambda_1) + [\varepsilon_{HbO2}(\lambda_2) - \varepsilon_{Hb}(\lambda_2)]R}$$

Figure 7:
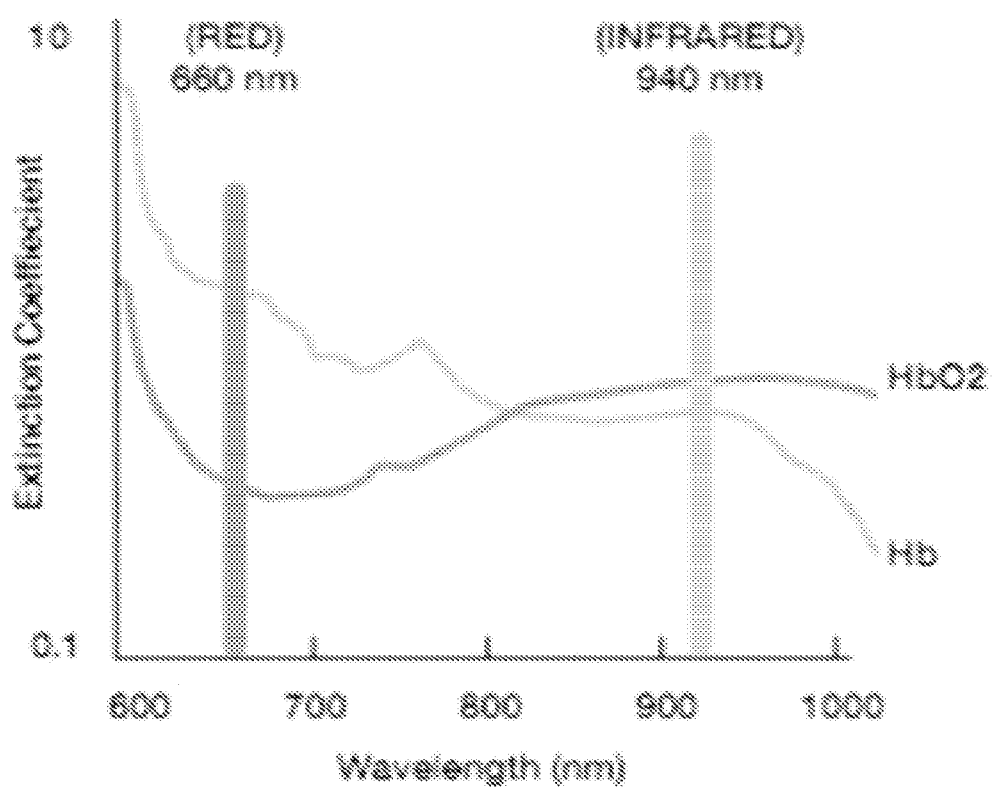
FIG. 7 shows a light spectrum of SpO2 sensing.

Referring to FIG. 7, typically $\lambda_1$ may be chosen as RED with wavelength of 660 nm and $\lambda_2$ chosen as INFRARED with wavelength of 940 nm. Having almost equal extinction coefficients for Hb and HbO2 for $\lambda_2$ (infrared) may allow denominator to play a lower role in the SpO2 computation. Having big difference in extinction coefficients for $\lambda_1$ (red) may allow SpO2 to change result in big variation of ratio.

Figure 8:
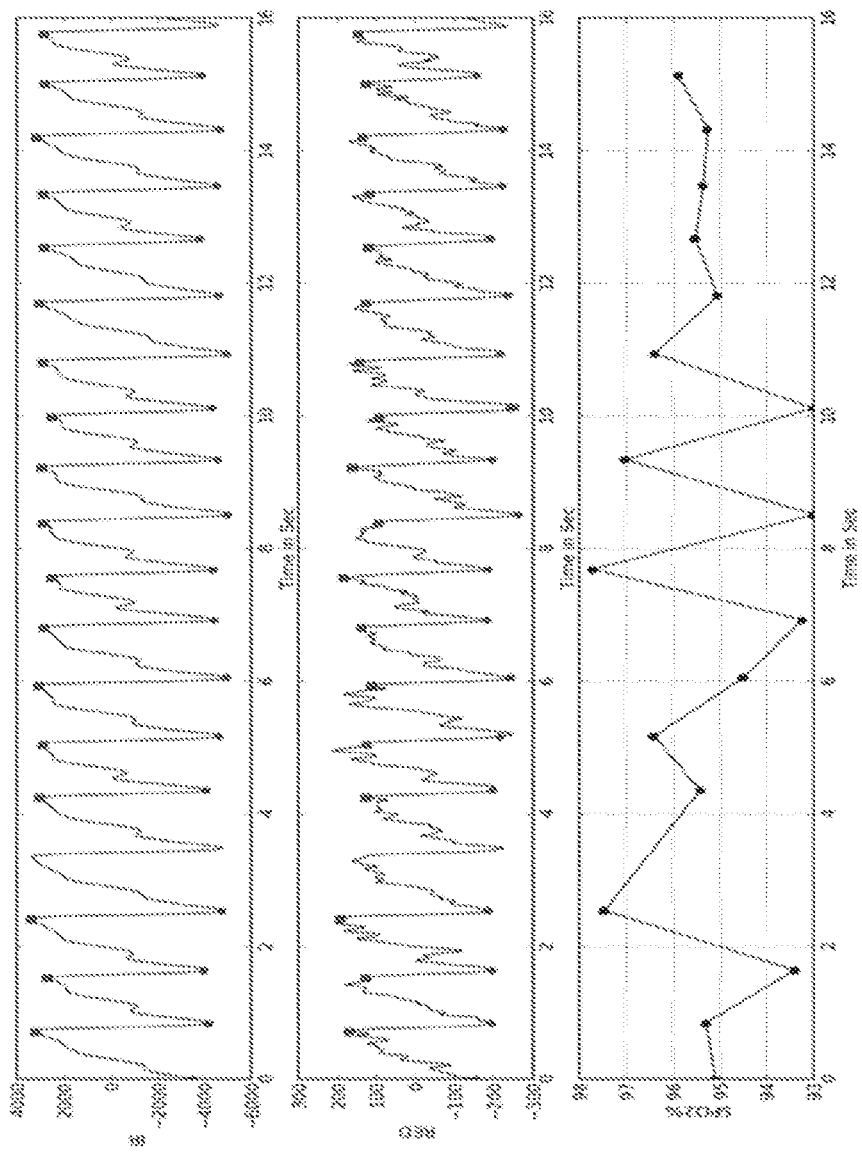
FIG. 8 shows results of an embodiment of evaluating SpO2 saturations with a ratio based method.

Using SpO2 sensor may comprise calibration. Using Beer-Lambert model may assume absorption of the light by blood. However, scattering may need to be factored in. An external calibrated device may be used for calibration. SpO2 may be described as a polynomial:

$$SpO2 = a + bR + cR^2$$

where a, b, c are best fit coefficients using a second order polynomial. Currently, a widely accepted equation may be SpO2=110+25R. FIG. 8 shows results of an embodiment of evaluating SpO2 saturations using the ratio based method.

Technologies disclosed herein may comprise an oximeter. An oximeter may comprise a motion resistant pulse oximeter. With motion, the pulsatile (AC) component may be extracted from arterial and nonarterial (venous) components. Pulse oximeter model as defined by Massimo is as follows:

$$IR = S + M$$

$$RD = R_a S + R_v M$$

where S is from pulsatile arterial blood, M is the motion signal from venous blood, $R_a$ is the ratio corresponding to arterial saturation (corresponding to SpO2), and $R_v$ is the ratio corresponding to venous saturation.

Further assumption may be that arterial signal and motion signal are uncorrelated. Correlations may be described as follows.

$$C_{rdrd} = \langle RD, RD \rangle = \langle S,S \rangle + \langle N,N \rangle + 2\langle S,N \rangle \approx$$
$$\langle S,S \rangle + \langle N,N \rangle$$

$$C_{rdir} = \langle RD, IR \rangle = R_a \langle S,S \rangle + R_v \langle N,N \rangle + 2R_a R_v$$
$$\langle S,N \rangle \approx R_a \langle S,S \rangle + R_v \langle N,N \rangle$$

$$C_{irir} = \langle IR, IR \rangle = R_a^2 \langle S,S \rangle + R_v^2 \langle N,N \rangle + (R_a + R_v)$$
$$\langle S,N \rangle \approx R_a^2 \langle S,S \rangle + R_v^2 \langle N,N \rangle$$

Relationship between the ratios $R_a$ and $R_v$ may be $$R_v = \frac{C_{rdrd} - c_{rdrd}R_a}{C_{rdir} - c_{irir}R_a} = f(R_a)$$

Define a reference signal and a reference motion signal:

$$RS = r_v IR - RD$$

$$RM = r_a IR - RD$$

For all $r_a \in SpO2\%$ range, $R_v = f(R_a)$. Find $r_a$ for which RS and RM have minimum correlation. Definition of a cost function may be $$T = \text{abs}[\text{angle}(RS(t), RN(t)) - \pi/2] + \sum_{\tau=1}^{n} \text{abs}[\text{angle}(RS(t), RN(t+\tau)) - \pi/2]$$

Figure 9:
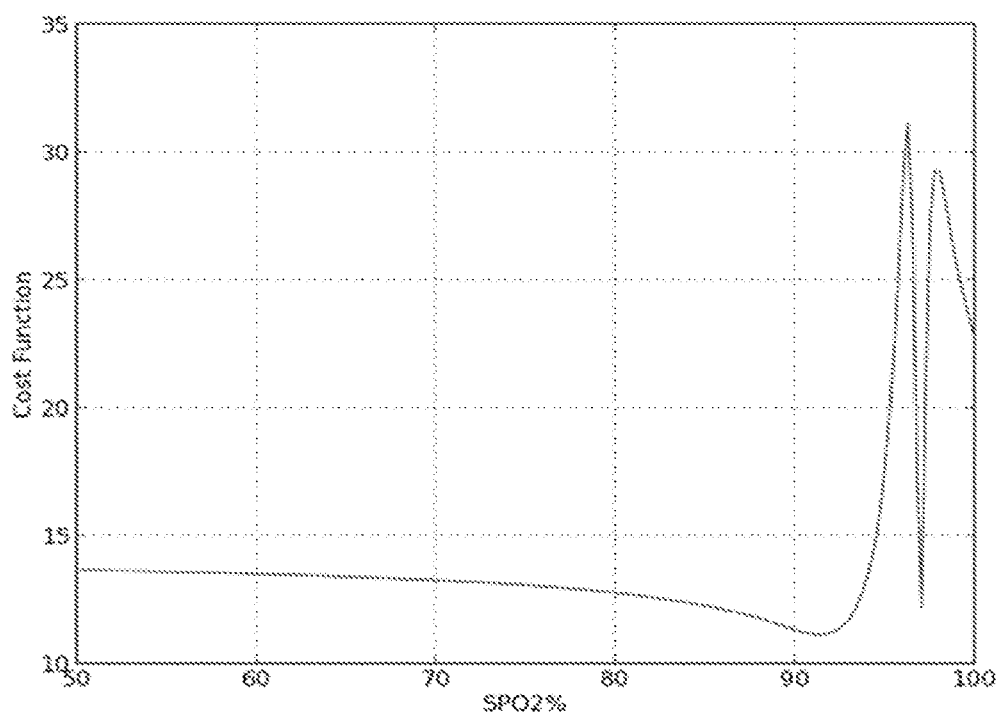
FIG. 9 shows an exemplary cost function plotted against SpO2 saturations.

An exemplary cost function plotted against SpO2 saturations is shown in FIG. 9.

Figure 10:
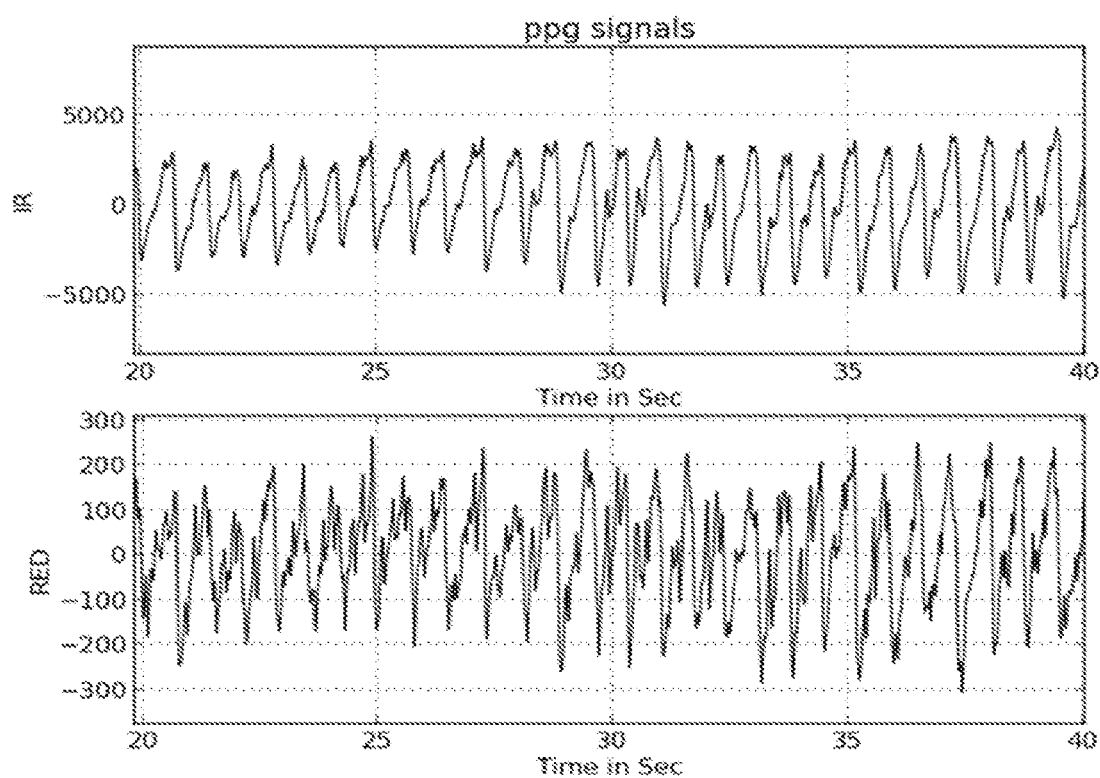
FIG. 10 shows exemplary SpO2 evaluation results obtained using a transmittance sensor on a finger; in this case, the plots show signals associated with infrared and red lights.
Figure 11:
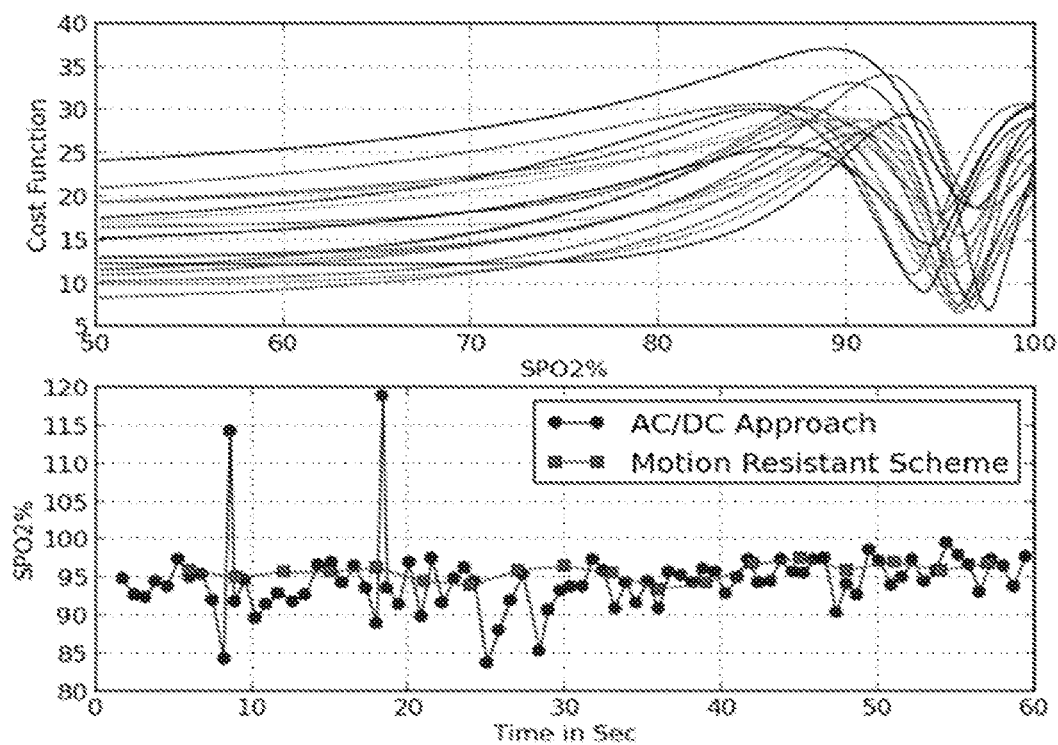
FIG. 11 shows exemplary SpO2 signal tracking and SpO2 cost functions obtained using a transmittance sensor on a finger.

FIG. 10 and FIG. 11 show exemplary results obtained using a transmittance sensor on a finger. FIG. 10 shows exemplary SpO2 evaluation results obtained using a transmittance sensor on a finger; in this case, the plots show signals associated with infrared and red lights. Specifically, FIG. 10 shows captured PPG waveform using a transmittance sensor on a finger using a Nellcor probe. FIG. 11 shows exemplary SpO2 evaluation results obtained using a transmittance sensor on a finger; in this case, the plots show the cost function and the SpO2 percentage. Specifically, FIG. 11 shows the results obtained using the transmittance sensor on a finger with the Nellcor probe of FIG. 10.

Figure 12:
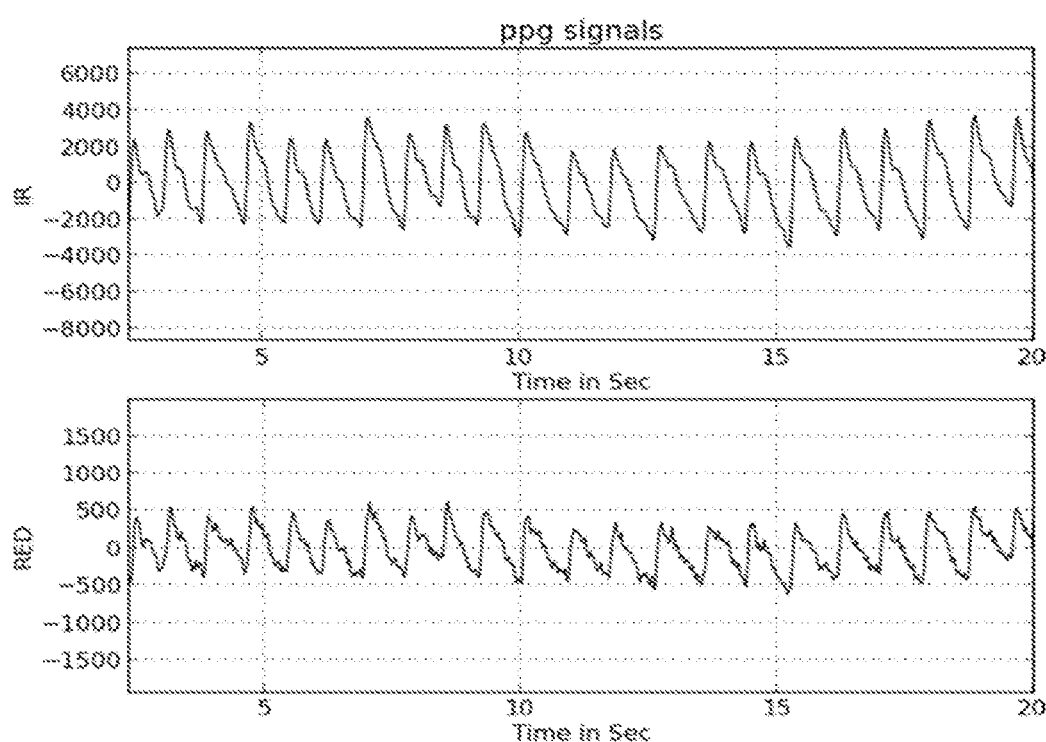
FIG. 12 shows exemplary SpO2 evaluation results obtained using a reflectance sensor on a finger; in this case, the plots show signals associated with infrared and red lights.
Figure 13:
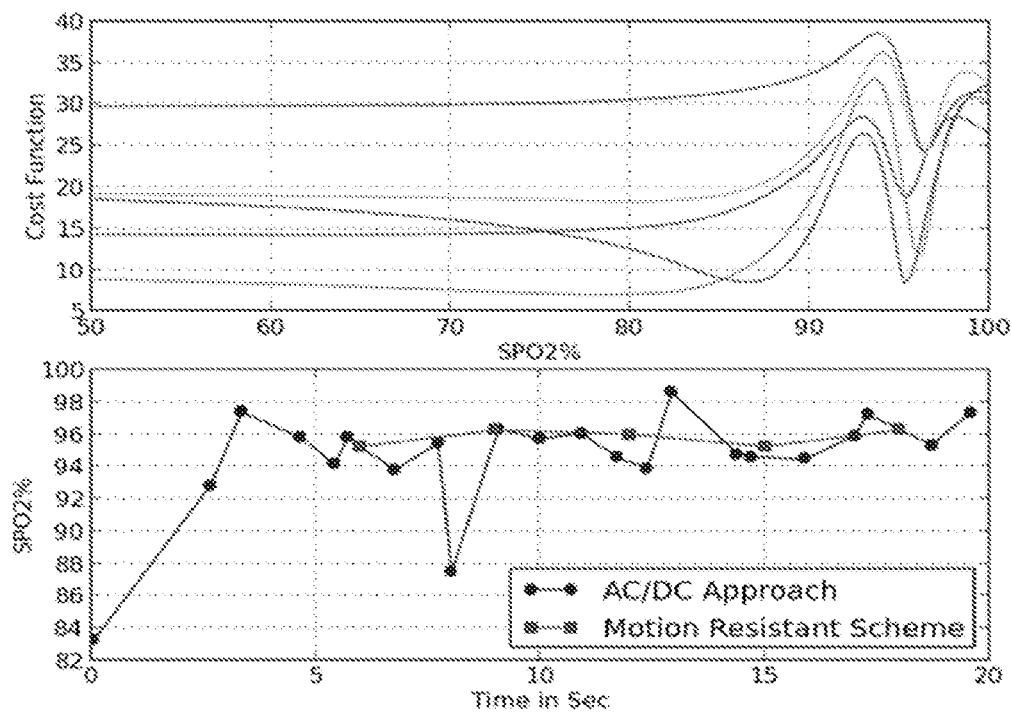
FIG. 13 shows exemplary SpO2 signal tracking and SpO2 cost functions obtained using a reflectance sensor on a finger.

FIG. 12 and FIG. 13 show exemplary results obtained using a reflectance sensor on a finger. FIG. 12 shows exemplary SpO2 evaluation results obtained using a reflectance sensor on a finger; in this case, the plots show signals associated with infrared and red lights. Specifically, FIG. 12 shows captured PPG waveform using a reflectance sensor on a finger using an APM part. FIG. 13 shows exemplary SpO2 signal tracking and SpO2 cost functions obtained using a reflectance sensor on a finger. Specifically, FIG. 13 shows the results obtained using the reflectance sensor on a finger with the part of FIG. 12.

Figure 14:
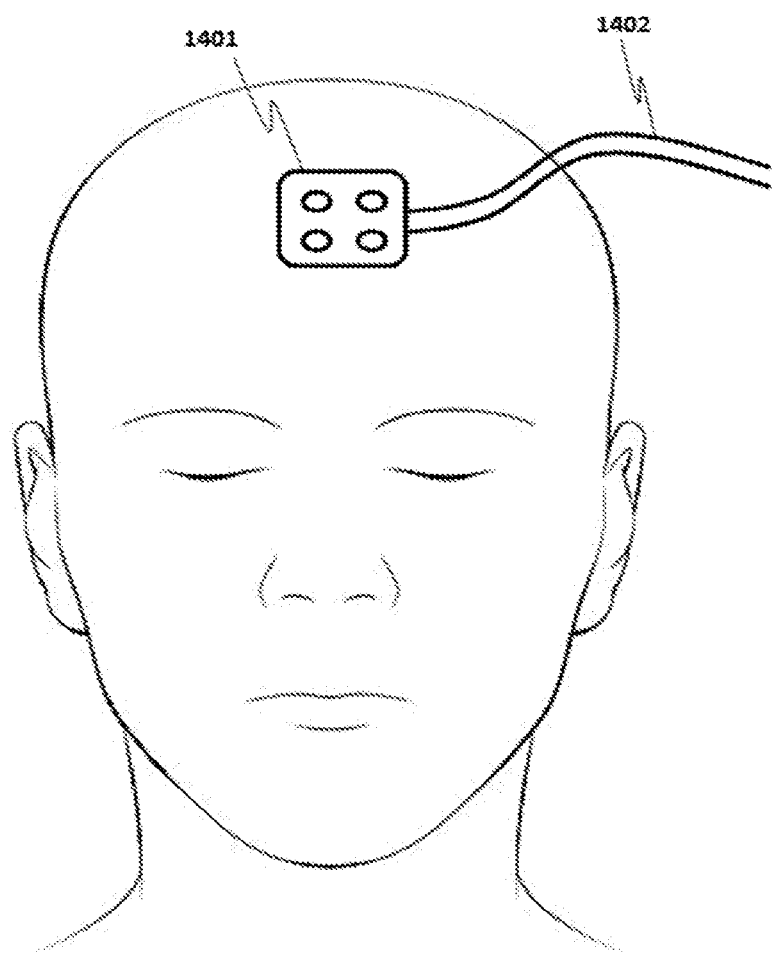
FIG. 14 shows an embodiment with a reflectance sensor on a forehead.
Figure 15:
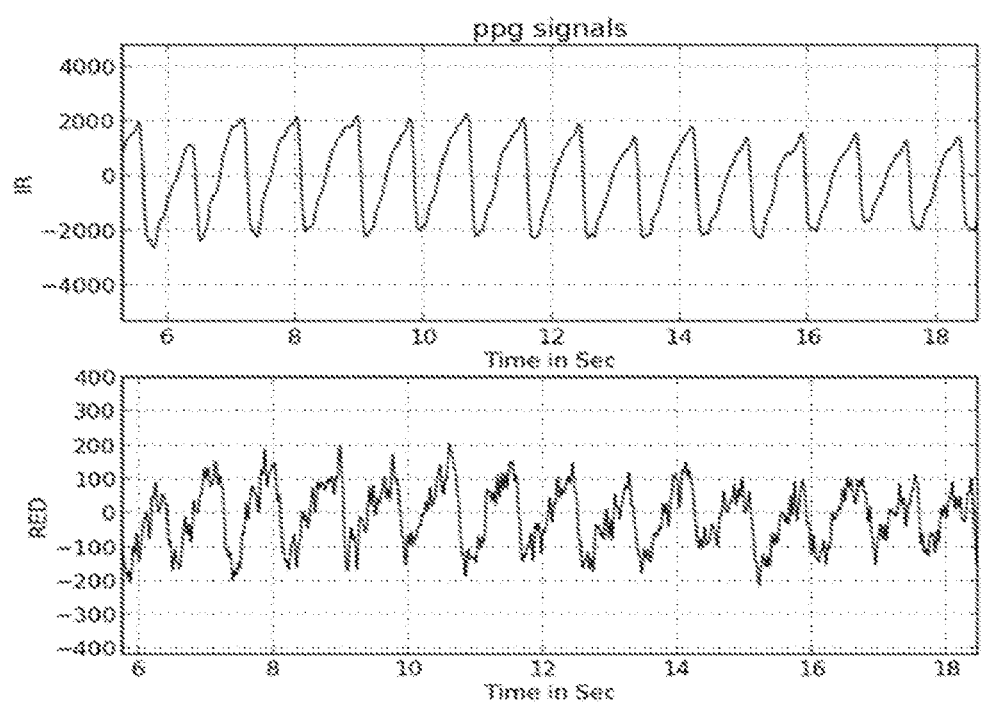
FIG. 15 shows exemplary SpO2 evaluation results obtained using a reflectance sensor on a forehead; in this case, the plots show signals associated with infrared and red lights.
Figure 16:
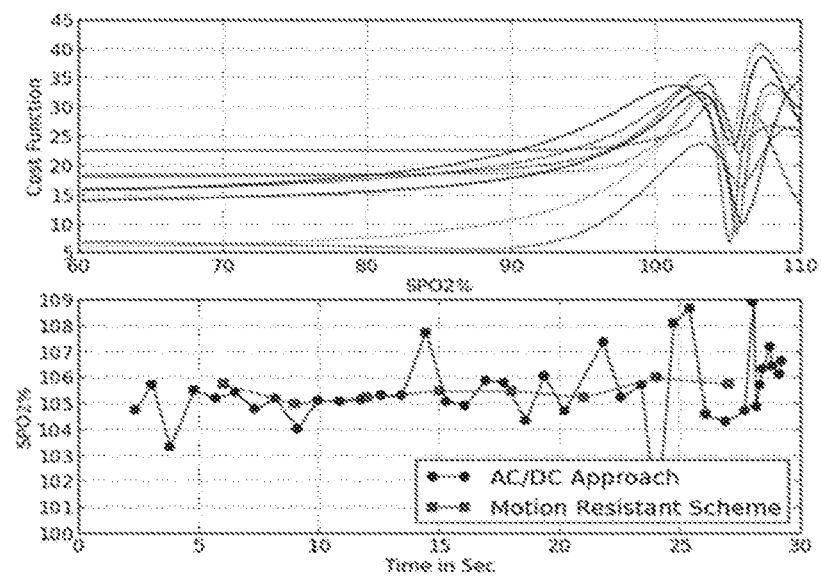
FIG. 16 shows exemplary SpO2 signal tracking and SpO2 cost functions obtained using a reflectance sensor on a forehead.

FIG. 14 shows an example of using a reflectance sensor 1401 on a forehead. In this case, a sensor 1401 is connected with another data collection device via an optional cable 1402. FIG. 15 and FIG. 16 show exemplary results the forehead embodiment. FIG. 15 shows exemplary SpO2 evaluation results obtained using a reflectance sensor on a forehead; in this case, the plots show signals associated with infrared and red lights. Specifically, FIG. 15 shows captured PPG waveforms using a reflectance sensor on a forehead using a Nonin sensor. FIG. 16 shows exemplary SpO2 signal tracking and SpO2 cost functions obtained using a reflectance sensor on a forehead. Specifically, FIG. 16 shows the results obtained using the reflectance sensor on the forehead using the Nonin sensor of FIG. 15.

Figure 17:
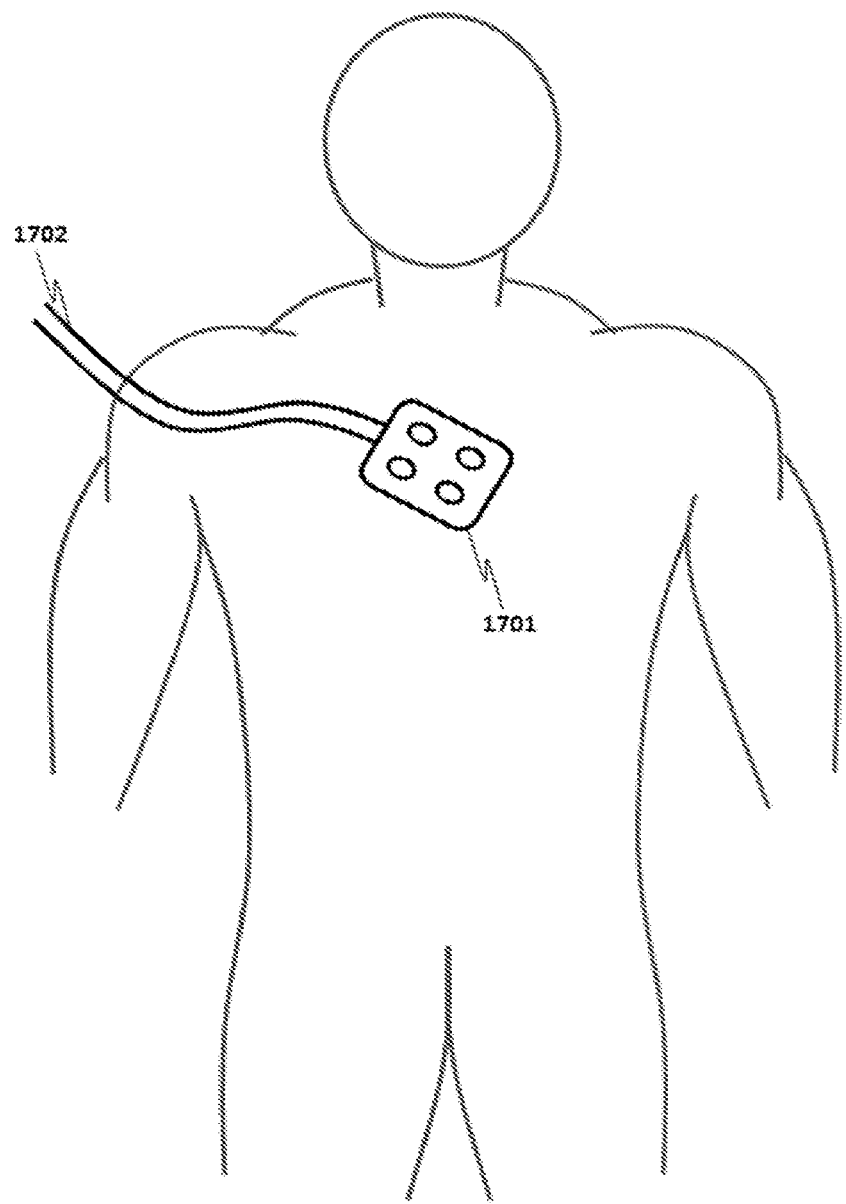
FIG. 17 shows an embodiment with a reflectance sensor on a chest.
Figure 18:
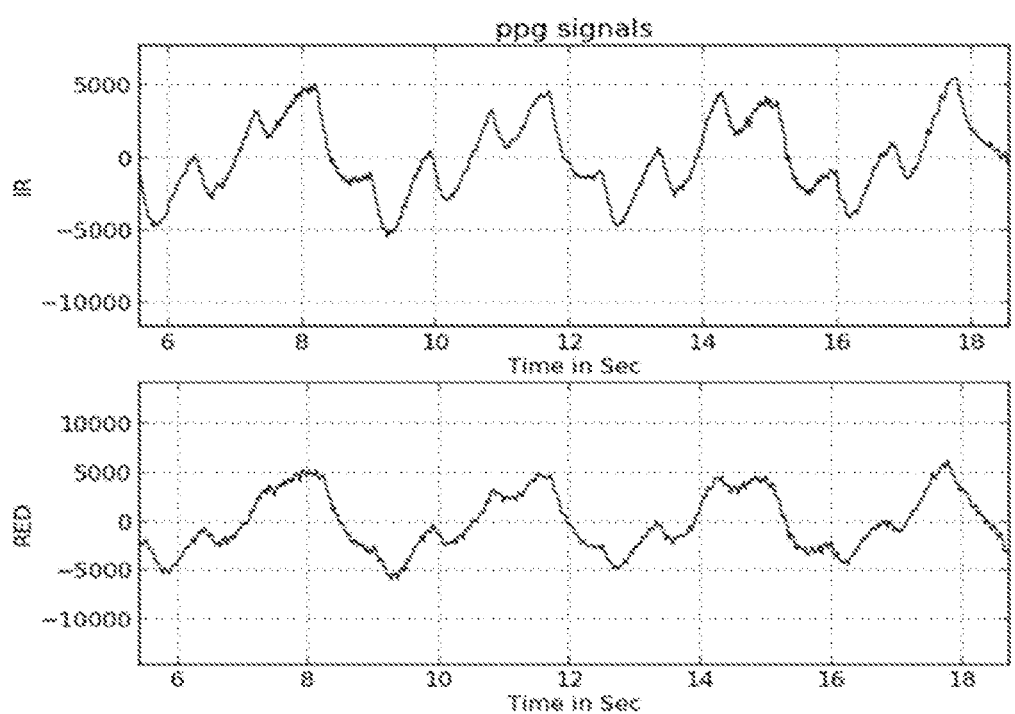
FIG. 18 shows exemplary SpO2 signal tracking obtained using a reflectance sensor on a chest; in this case, the plots show signals associated with infrared and red lights.
Figure 19:
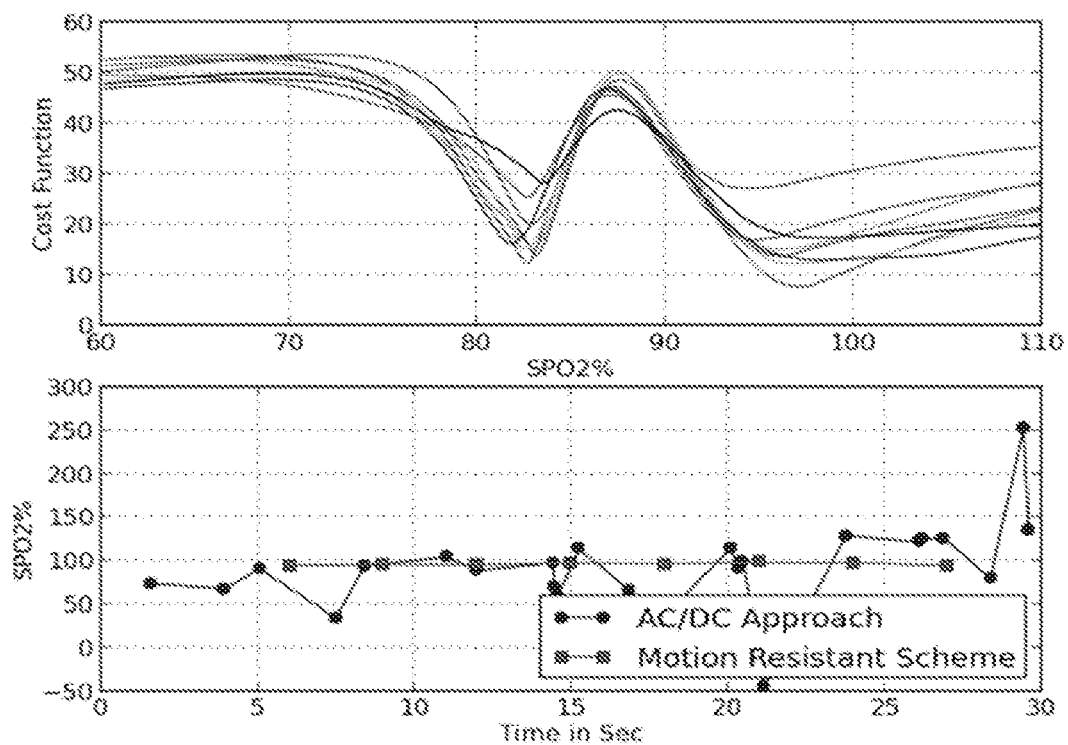
FIG. 19 shows exemplary SpO2 signal tracking and SpO2 cost functions obtained using reflectance sensor on a chest.

FIG. 17 shows an example with a reflectance sensor 1701 on a chest via an optional cable 1702 to measure SpO2. FIG. 18 shows exemplary SpO2 signal tracking obtained using a reflectance sensor on a chest; in this case, the plots show signals associated with infrared and red lights. Specifically, FIG. 18 shows captured PPG waveforms using a reflectance sensor on a chest using an APM part. FIG. 19 shows exemplary SpO2 signal tracking and SpO2 cost functions obtained using reflectance sensor on a chest. Specifically, FIG. 19 shows the results obtained using the reflectance sensor on the chest using the APM part of FIG. 18.

In general, examples show good results from reflectance sensor on finger, forehead and chest. Further, reduction of computations in motion resistant scheme is observed. The system may get an algorithm for heart rate computation from photoplethysmographic (PPG) signal in motion conditions.

Data Collection Device

The technologies disclosed herein may comprise a data collection device in wireless communication with a patch. A data collection device may be used to receive signals collected by a patch. A data collection device may temporarily store signals for a period, or immediately relay the signals to another wireless access point or a server.

A data collection device may be in a small size. A data collection device may comprise a maximum dimension equal to or smaller than 8 cm, 9 cm, 10 cm, 11 cm, 12 cm, 13 cm, 14 cm, 15 cm, 16 cm, 17 cm, 18 cm, 19 cm, or 20 cm.

The weight of a data collection device may be equal or less than 1 gram, 2 grams, 3 grams, 4 grams, 5 grams, 6 grams, 7 grams, 8 grams, 9 grams, 10 grams, 11 grams, 12 grams, 13 gram, 14 grams, 15 grams, 16 grams, 17 grams, 18 grams, 19 grams, 20 grams, 21 gram, 22 grams, 23 grams, 24 grams, 25 grams, 26 grams, 27 grams, 28 grams, 29 grams, 30 grams, 31 gram, 32 grams, 33 grams, 34 grams, 35 grams, 36 grams, 37 grams, 38 grams, 39 grams, 40 grams, 41 gram, 42 grams, 43 grams, 44 grams, 45 grams, 46 grams, 47 grams, 48 grams, 49 grams, 50 grams, 60 grams, 70 grams, 80 grams, 90 grams, 100 grams, 110 grams, 120 grams, 130 grams, 140 grams, 150 grams, 160 grams, 170 grams, 180 grams, 190 grams, or 200 grams.

The thickness of a data collection device may be equal or less than 0.1 inches, 0.2 inches, 0.3 inches, 0.4 inches, 0.5 inches, 0.6 inches, 0.7 inches, 0.8 inches, 0.9 inches, 1 inch, 2 inches, 3 inches, 4 inches, or 5 inches.

A data collection device may comprise a volume equal to or smaller than 5 $cm^3$, 10 $cm^3$, 15 $cm^3$, 20 $cm^3$, 25 $cm^3$, 30 $cm^3$, 35 $cm^3$, 40 $cm^3$, 45 $cm^3$, 50 $cm^3$, 60 $cm^3$, 70 $cm^3$, 80 $cm^3$, 90 $cm^3$, 100 $cm^3$.

A data collection device may be configured to receive the monitored physiological data from the patch. A data collection device may comprise a wireless communication unit to communicate with a patch. The wireless communication mechanism may comprise one or more of the following: a near range communication means, a short range communication means, and a long range communication means. A wireless communication unit may operate on one or more of the following protocols: a Bluetooth protocol, a Wi-Fi protocol, an ultra-wide band protocol.

The light weight, small dimension and wireless communication of a data collection device may provide various benefits. One exemplary benefit is that a data collection device may be portable or allow a user to easily carry the patch and a data collection device; for example, a user may attach a patch on his chest and place a data collection device in his pocket. Another exemplary benefit allows a user to use the system on a daily basis. Another exemplary benefit is low energy consumption. Another exemplary benefit is easy configuration. Another exemplary benefit is no worry about wiring when the patch and the data collection device communicate wirelessly each other.

A shape of a data collection device may be in a form of a card. In some examples, a data collection device can be in a form of a wrist band, a pendant, a pen, a phone, a key, a keychain, and a pair of glasses.

A data collection device may comprise a memory. A data collection device may be capable of storing physiological data measured from the user for at least two days or more. Alternatively, the storage may hold physiological data for at least 1 hour, 2 hours, 3 hours, 4 hours, 5 hours, 6 hours, 7 hours, 8 hours, 9 hours, 10 hours, 11 hours, 12 hours, 24 hours, 36 hours, 48 hours, 60 hours, 72 hours, 84 hours, 96 hours, 108 hours, 120 hours, 132 hours, or 144 hours.

A data collection device may be configured for Holter monitoring, event monitoring, and/or loop monitoring. In some embodiments, a data collection device may be used in an ambulatory setting to monitor a subject's physiological signals, e.g., ambulatory cardiac monitoring procedures. In Holter monitoring, a data collection device can automatically choose a 2 or 3 day option for continuously monitoring various electrical activity of cardiovascular system lasting more than 48 hours or 72 hours. In event monitoring, a data collection device may be triggered to monitor an event (e.g., surgery, a stroke, a treatment, etc.); in some cases, the device may be triggered by an event to collect physiological data;

the device may collect few minutes of instant data of an event, followed by sending the data to a server. Event monitoring may allow a user to flag or press a button on occurrence of an event, followed by transmitting few minutes of data to a wireless access point or a relaying device.

In the case of looping monitoring, a patch of electrodes may be attached to a wrist, a finger, and/or a chest. A data collection device may be triggered to collect data up to 30 minutes. A data collection device may collect and record several minutes at a time, then starts over. A data collection device may save the recordings, or further transmit the recordings to a wireless access point, a relay device, or a server.

A data collection device may involve data relaying. In some cases, data file transfer to cloud or another Wi-Fi enabled device may be carried after data collection is done. A data collection device may operate only in data collection mode. Other examples may include an ability to port an application for on-card analytics or any pre-processing of data collected before it is transferred to another device for subsequent processing. A data collection device may be configured to support store and forward to cloud or another device in real time when enabled. A data collection device may not involve in data analytics, but only support data collection in various modes needed in various monitoring procedures.

A data collection device may be configured to store and/or transmit the received physiological data to another device or a server in real time.

A data collection device may be configured to transmit the received physiological data to another device or a server after data collection is completed. Data collection may be related to Holter monitoring, event monitoring, and/or loop monitoring. In some applications, data collection may be based on a biological cycle, e.g., a cardiac cycle, a respiration cycle, a 24-hour period, etc.

A data collection device may be configured to transmit the received physiological data to another device or a server in batch file. An exemplary benefit of batch-mode transmission is to allow a data collection device unnecessary to maintain wireless communication all the time. In some applications, a user carrying a data collection device may be out of the range of wireless communication.

A data collection device may not be configured to analyze the received physiological data.

A data collection device may be configured to track a location of the user. Tracking a location may allow a system to evaluate an environment of a user, and may further calibrate the patch and data collection device.

A data collection device may comprise a GPS. Alternatively or in addition, the data collection device may comprise accelerometers and/or gyroscope sensors. Output of the sensors (e.g. accelerometers or gyroscopes) may be integrated to provide a location of the data collection device such that its location may be tracked.

A data collection device may comprise a user interface. A user interface may allow a user to configure, or to communicate with, a patch. A user interface may allow a user to configure the data collection device. A user interface may allow a user to set up a scenario of use. A user interface may comprise one or more buttons. Actuation of the one or more buttons may signal a beginning of an event for event monitoring. Actuation of the one or more buttons may be configured to record and store a message from the user in the data collection device with aid of a microphone. A user interface may comprise a touch-screen display. A data collection device may comprise a microphone. A user interface may comprise an "On" button that starts data collection. A user interface may comprise an "Event" button to press if user experiences a symptom (stamp data before and after the symptom is flagged). When Event occurs, the device is configured to record an associated voice message. A user interface may comprise a "Transfer" data button, wherein collected data for the selected clinical procedure is transferred to the cloud after procedure is complete (Holter, Event or Loop). A user interface may comprise a "Real-time" monitoring button: when pressed data is continuously stored and forwarded to cloud continuously whenever connected.

A data collection device may be configured to communicate with a mobile device. A mobile device may be a cellphone, a personal digital assistant (PDA), and/or a tablet.

A data collection device may be configured to communicate with a patient monitor. A data collection device may be configured to communicate with the patient monitor with aid of an adapter.

A data collection device may be further configured to communicate with two or more different types of devices. The two or more different types of devices may comprise a patient monitor and a mobile device.

A data collection device may communicate with a patch via Wi-Fi, MBand, and/or UWB. A patch may further be configured to communicate with a third device. A patch may be configured to communicate with the third device via the data collection device. A data collection device may extend a communication distance for the patch to communicate with the third device. A data collection device may extend the communication distance between the patch and the third device by at least 2 times as compared to not having the data collection device. In various embodiments, extension of the communication distances may be at least 1.5 times, 2 times, 2.5 times, 3 times, 3.5 times, 4 times, 4.5 times, and 5 times. In a hospital monitoring system, a data collection device may communicate with a patient monitor, or a wireless access point, or a mobile phone, or a combination thereof; based on the dynamic communication setting, a data collection device may tentatively store collected physiological data or may server as a relaying device. The physiological data may be further transmitted to a server for analytics to extract useful information for a healthcare provider. There wireless communication options such as WiFi, M-Band and UWB may be user customizable. Any combination of these radios may be user configurable. Optionally, the data collection device may receive ECG, Respiration, SpO2, temperature and location measurements or interact with the foregoing technologies that are user customizable. Any combination of these elements may be user configurable.

Figure 22:
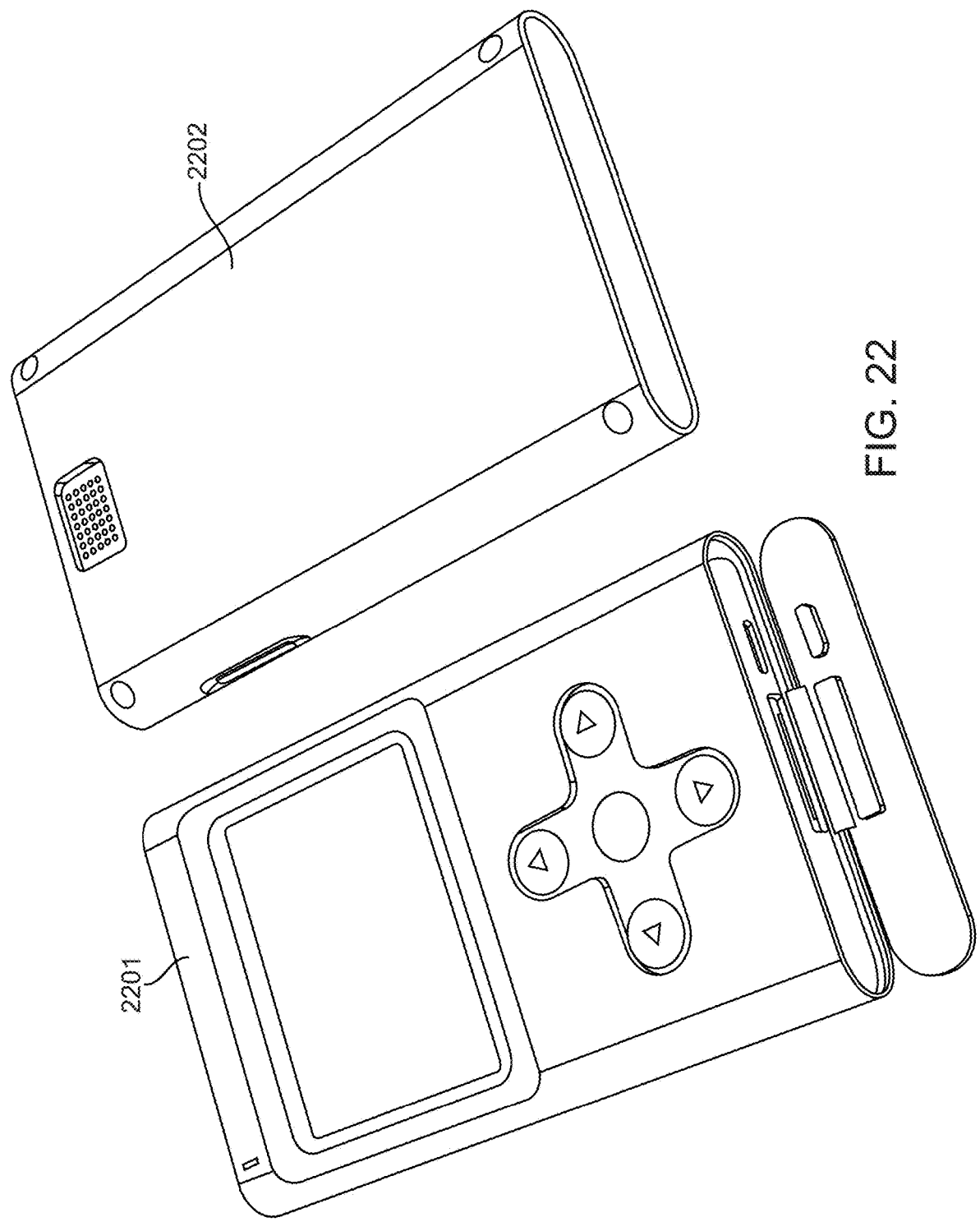
FIG. 22 illustrates a design of a data collection device.

FIG. 22 illustrates a design of a data collection device. The data collection device may comprise any or all of the features described elsewhere (e.g., with respect to data collection device 512 of FIG. 5). The data collection device may have a front side 2201 and a back side 2202. The data collection device may provide a simple user interface. The data collection device may comprise a screen for displaying information and/or buttons.

Figure 23:
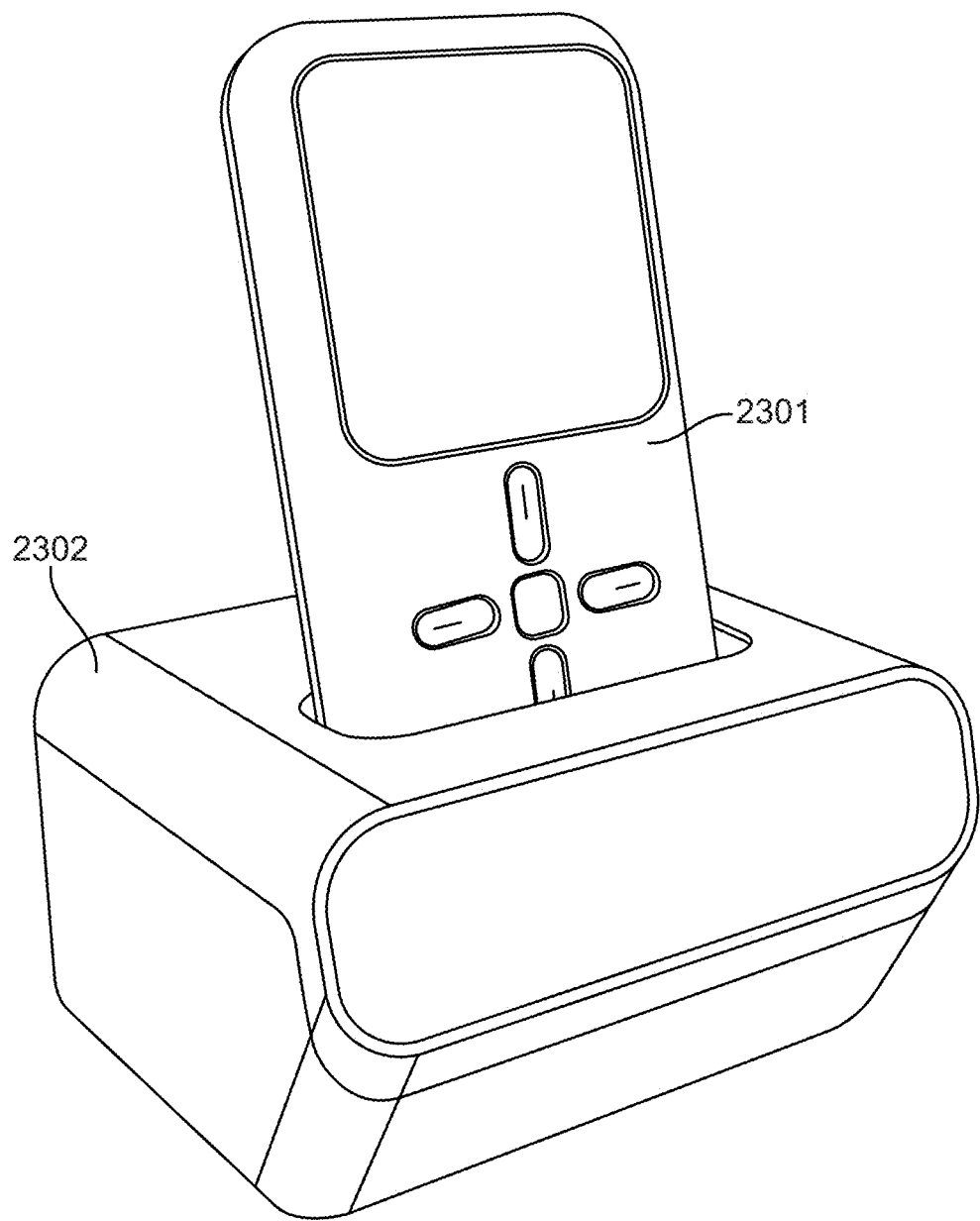
FIG. 23 illustrates a perspective view of a data collection device coupled with an adapter.
Figure 24:
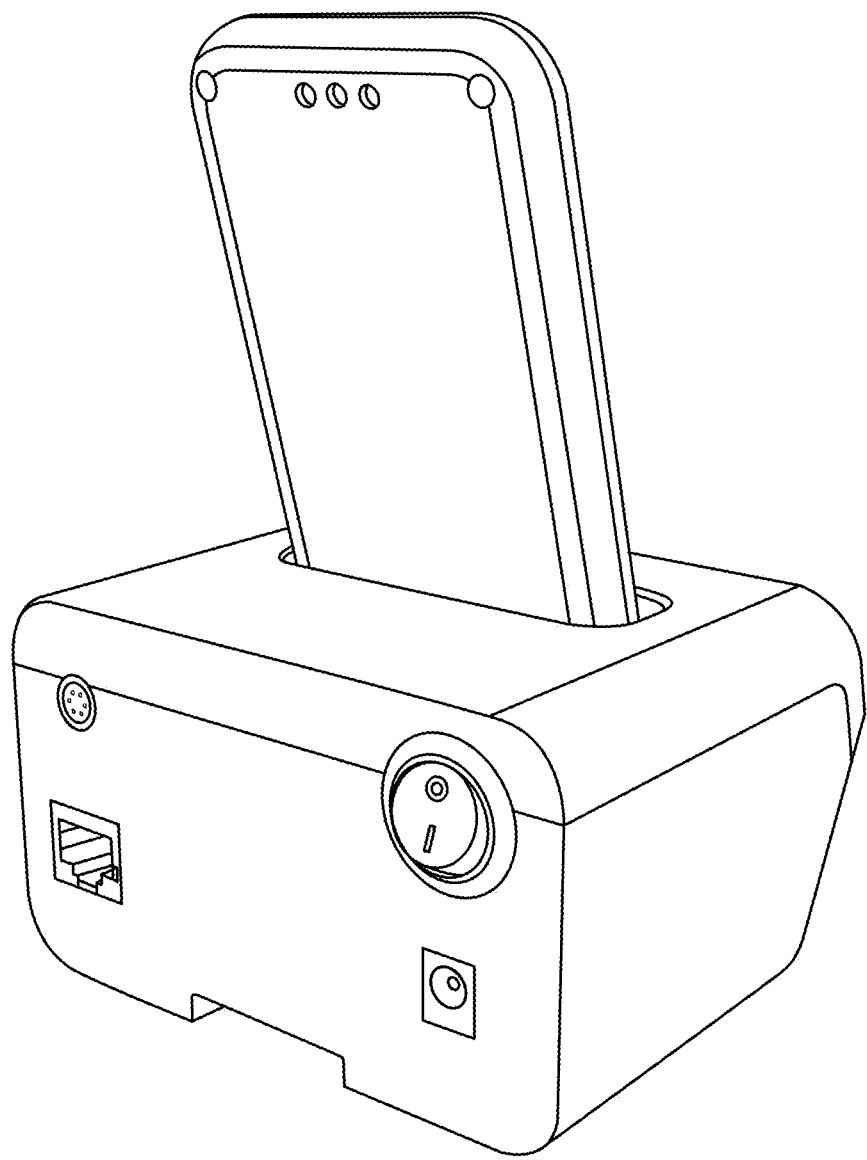
FIG. 24 illustrates a different perspective view of a data collection device coupled with an adapter.

In some instances, the data collection device may be operably coupled to an adapter, substantially described elsewhere herein. FIG. 23 illustrates a perspective view of a data collection device 2301 coupled with an adapter 2303. In some instances, the data collection device may be docked into a base unit such as the adapter. The data collection device and the adapter may comprise complementary ports, or mating mechanisms. The adapter may be connected to a legacy patient monitor. The combined unit may leverage the hardware of both the data collection device and/or the adapter. The adapter may in some instances collect incoming data from a data collection device. For example, the data collection device may have collected or may collect data from a patch sensing physiological signals from a user. The adapter may relay such data subsequently to a patient monitor (e.g. bedside monitor) connected to the adapter, e.g. via cable. This scheme may allow convenient and easier pairing of a patch with the patient monitor and/or the adapter. For example, the adapter may be attached to a patient monitor cable (e.g. via cable) and not be easily removed. The data collection device however may be lifted from the adapter and be able to be brought closer to a patch worn by a patient in order to greatly help a pairing process. In some instances, such a scheme may allow a user to move untethered to a patient monitor while relevant physiological signals are being collected by the data collection device. The relevant physiological signals may subsequently be viewed on a patient monitor via the adapter. FIG. 24 illustrates a different perspective view of a data collection device coupled with an adapter.

The data collection device may be utilized as part of a healthcare monitoring system, described throughout. For example, the data collection device and the adapter may be utilized as part of the integrated monitoring system referred to in FIG. 5. In some instances, the healthcare monitoring system may further comprise a server configured to receive the physiological data signals, and the server (or other processors) may be configured to perform analytics on the physiological data.

Defibrillation Protection

Traditional defibrillation protection schemes may be bulky and not practical to implement in body worn vital signal sensors, such as the patches or data collection device disclosed herein. As disclosed throughout, the technologies may comprise miniaturized protection circuitry to provide protection to the user, patch, or various other components. For example, defibrillation may be applied to a patient while the patient wears devices like the patch, e.g. in an emergency room or ambulance. A voltage pulse from a defibrillator can have peak voltage above 240V, 300V, 400V, 500V, 600V, 700V, 800V, 900V, 1 kV, 2 kV, 3 kV, 4 kV, 5 kV, 6 kV, 7 kV, 8 kV, 9 kV, or 10 kV. Further, a voltage pulse may last for more than 1 millisecond (ms), 2 ms, 3 ms, 4 ms, 5 ms, 6 ms, 7 ms, 8 ms, 9 ms, 10 ms, 20 ms, 30 ms, 40 ms, 50 ms, 60 ms, 70 ms, 80 ms, 90 ms, 100 ms, 200 ms, 300 ms, 400 ms, 500 ms, 600 ms, 700 ms, 800 ms, 900 ms, or 1000 ms. During such an event, a patch disclosed herein may comprise miniaturized protection circuitry and may not be impacted and/or damaged by the defibrillation voltage shocks. Optionally, the patch may tolerate the voltage shocks and/or recover to continue its function. In some instances, the patch may be configured to satisfy various safety requirements, e.g. the safety requirement of IEC60601. Examples of safety requirements include, but are not limited to, prevent electric shocks, energy hazards, fire, heat related hazards, radiation, mechanical hazards, and chemical hazards.

Optionally, the disclosed patch, data collection device, or various other components may comprise defibrillation prevention circuitry to avoid not only electrical shocks but also electrical leakage and radiation when a defibrillation procedure is applied on a subject. With the defibrillation protection, the patch, data collection device or various other components may maintain their normal functionalities of monitoring a subject's physiological signals and transmitting the data. For example, during a defibrillation event, it may be beneficial if effects of the defibrillation procedure is not affected by devices on a person. For example, it may be beneficial for a patch or a data collection device on a user does not alter or affect a defibrillation procedure.

Figure 20:
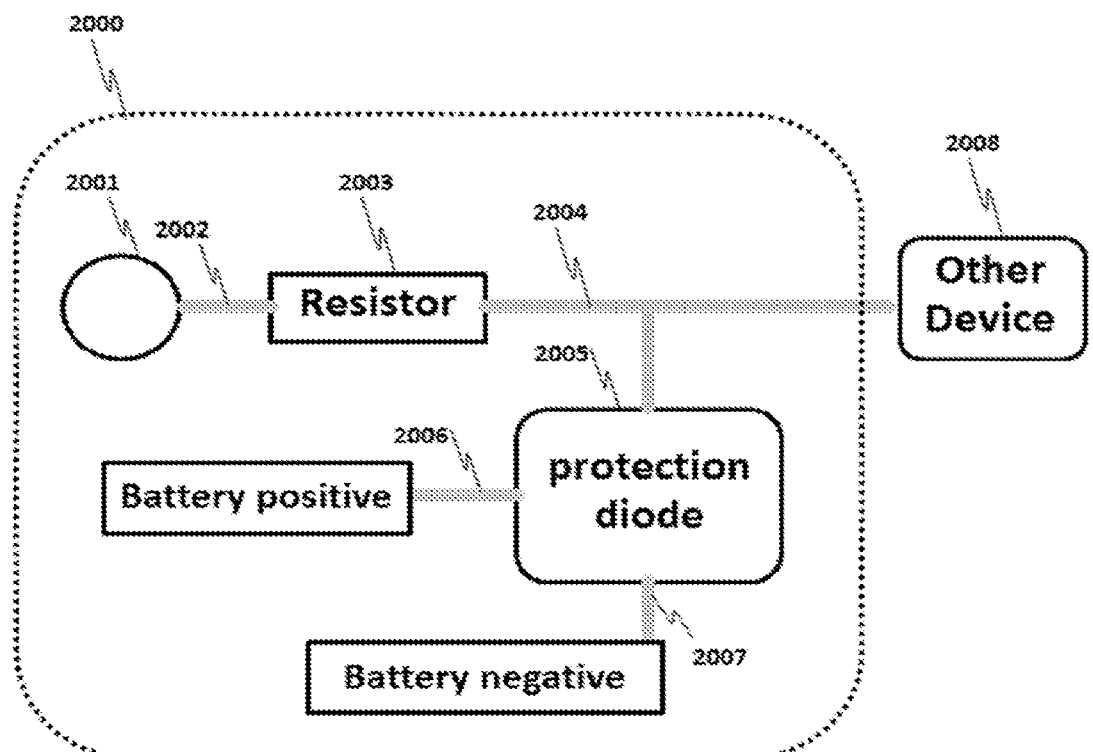
FIG. 20 shows exemplary protection circuits utilized with a patch.

FIG. 20 shows exemplary protection circuits utilized with a patch and able to protect defibrillation shocks. The circuitry may be an independent module, or part of a patch. The disclosed circuitry may be integrated into a patch as described throughout the disclosure, e.g. as shown in FIGS. 2A and 2B. Some, or all of the illustrated circuitry of FIG. 20 may correspond to elements previously discussed herein. For example, electrode 201 of FIG. 2A may correspond to electrode 2001 of FIG. 20 while resistor 212 of FIG. 2A may correspond to resistor 2003 of FIG. 20. The circuitry may comprise an electrode assembly 2001 which can be configured to be in contact with a patient's body. The circuitry may comprise electrical interconnect 2002 coupling an electrode 2001 to a resistor 2003. The circuitry may comprise electrical interconnect 2004 from a resistor 2003 to a protection diode 2005 and other components 2008. An example of other components 2008 may include a system-on-chip (SOC) component. An SOC component may comprise a sensing circuit. The circuitry 2000 may comprise a battery, with electrical interconnect 2006 coupling a battery positive to a protection diode 2005 and electrical interconnect 2007 coupling a battery negative to the protection diode 2005.

Referring again to FIG. 20, choices of resistor 2003 may be based on various considerations. When a defibrillator is applied, the voltage can be sensed by one or more electrodes 2001 which are in contact with the patient body. This may result in a voltage of above a voltage threshold at the input of the resistor 2003. Optionally, the defibrillation may be sensed by the one or more electrodes and result in a voltage equal to or more than about 1 kV, 1.5 kV, 2 kV, 2.5 kV, 3 kV, 3.5 kV, 4 kV, 4.5 kV, 5 kV, 5.5 kV, 6 kV, 6.5 kV, 7 kV, 7.5 kV, 8 kV, 8.5 kV, 9 kV, 9.5 kV, or 10 kV at the input of the resistor, also referred to herein as a safety resistor. The safety resistor 2003 may be selected to handle various peak pulse voltages. In some instances, the resistor may be configured to handle peak pulse voltages equal to or more than about 1 kV, 1.5 kV, 2 kV, 2.5 kV, 3 kV, 3.5 kV, 4 kV, 4.5 kV, 5 kV, 5.5 kV, 6 kV, 6.5 kV, 7 kV, 7.5 kV, 8 kV, 8.5 kV, 9 kV, 9.5 kV, or 10 kV. Any type of resistor may be provided. In some instances, a thick film resistor may be provided for higher pulse voltages. Optionally, a type or size of the resistor may be selected based on envisioned use of the patch and/or circuitry. For example, a thick film resistor may be provided for a patch that is foreseeably used for a patient who may undergo defibrillation while a different type of resistor may be provided for patients who may not foreseeably undergo defibrillation. For example, a resistor capable of handling 5 kV peak pulse voltages may be provided for a patient who may undergo defibrillation while a resistor capable of handling other peak pulse voltages may be provided for patients who may not foreseeably undergo defibrillation.

In some instances, a physical size of the safety resistor 2003 may be a relevant consideration to ensure that protection is provided to the user, patch, or other components. In some instances, a physical size of the safety resistor may be a relevant consideration to ensure the patch and/or other components being protected from the application of a procedure such as defibrillation. A factor of physical size may be a creepage distance, which is the shortest path between two conductive parts (or between a conductive part and the bounding surface of the equipment) measured along the surface of the insulation. A certain minimum distance (e.g., at least 1 mm, at least 2 mm, at least 3 mm, at least 4 mm, at least 5 mm, at least 6 mm, at least 7 mm, at least 8 mm, at least 9 mm, at least 10 mm) may be maintained between two terminals of the safety resistor 2003. Options of resistors include rectangular surface mount resistors and axial resistors. Surface mount resistors are characterized by codes, e.g., 0201, 0402, 0603, 0805, 1206, 1210, 1218, 2010, and 2512, where the greater the code, a larger size and a higher resistance a resistor has. In some cases, a safety resistor 2003 with code number 2512 or above may be used. A resistor with code number 2512 or higher may be also suitable for higher power tolerance and therefore may be employed as a safety resistor herein. The value of the resistor 2003 may be selected such that there is an enough voltage drop across the resistor 2003 and meanwhile the voltage may not load the defibrillator. In some applications, a safety resistor of at least 1 k Ohm, 2 k Ohm, 3 k Ohm, 4 k Ohm, 5 k Ohm, 6 k Ohm, 7 k Ohm, 8 k Ohm, 9 k Ohm, 10 k Ohm, 15 k Ohm, 20 k Ohm, 25 k Ohm, 30 k Ohm, 35 k Ohm, 40 k Ohm, 45 k Ohm, or 50 k Ohm may be preferred. A resistor with 23.7 k Ohm or more may satisfy the electrical design.

Referring again to FIG. 20, interconnect 2002 between electrode 2001 and safety resistor 2003 may be PCB trace or insulated wire. The trace may be thick enough to tolerate the pulse peak voltage and introduce as less inductance as possible. A trace thickness may be at least 0.01 mm, 0.02 mm, 0.03 mm, 0.04 mm, 0.05 mm, 0.06 mm, 0.08 mm, 0.09 mm, 0.1 mm, 0.2 mm, 0.3 mm, 0.4 mm, or 0.5 mm. Further, some designs may avoid metal within a surrounding distance of an interconnect; examples of a minimum surrounding distance may be at least 1 mm, at least 2 mm, at least 3 mm, at least 4 mm, at least 5 mm, at least 6 mm, at least 7 mm, at least 8 mm, at least 9 mm, or at least 10 mm.

Figure 21:
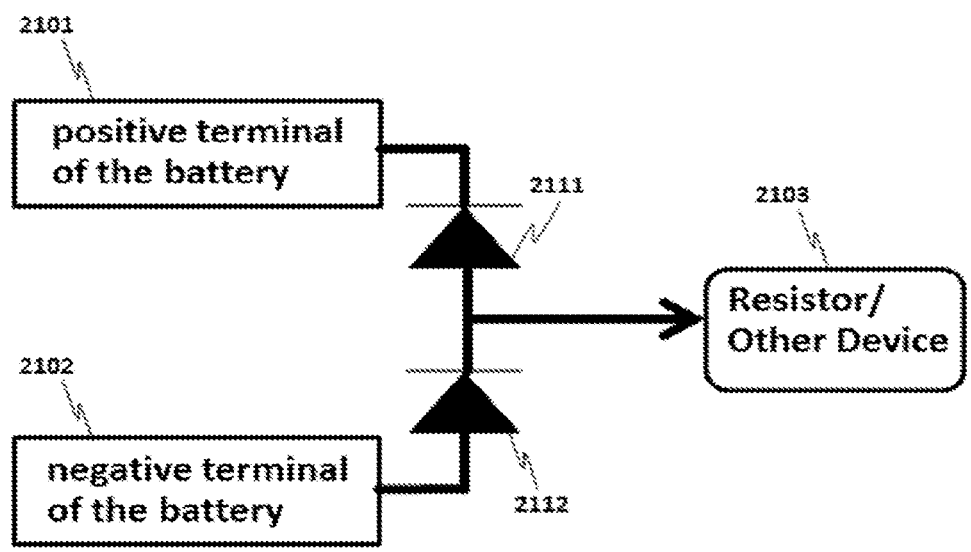
FIG. 21 shows exemplary safety diodes.

In some instances, a safety diode 2005 in FIG. 20 may be a relevant consideration to ensure that protection is provided to the user, patch, or other components. In some instances, a high speed and a high power diode may be selected. Referring to FIG. 21 which shows exemplary safety diodes, diodes 2111 and 2112 connected back to back may be assembled to form a safety diode. When a safety resistor is employed, the safety resistor can alleviate a voltage shock. For example, a voltage shock of above 1 kV, 2 kV, 3 kV, 4 kV, 5 kV, 6 kV, 7 kV, 8 kV, 9 kV, 10 kV can be reduced down to about 100V. When a safety diode is further employed, the reduced voltage may be clipped to highest battery voltage. On the other hand, the diodes 2111 and 2112 operatively coupled to an SOC device 2103 may rectify a voltage pulse seen by the SOC device 2103 to a battery voltage 2101. Similarly, on the negative terminal 2102, the diode can rectify the voltage pulse and also clips the voltage peak to negative terminal voltage of the battery. The rectified voltage can prevent the SOC device 2103 from electrical damages.

When a safety diode is conducting in a forward condition and immediately switched to a reverse condition, the diode may conduct in a reverse condition for a short switching time as the forward voltage bleeds off. Typically, during the reverse condition, the electric current may be still large and may impact other circuitry. To avoid the impact of electrical shocks taking place during the reverse condition, the diode with fast switching and recovery time may be selected. A selected diode may have a switching and recovery time below 1 nanosecond (ns), 2 ns, 3 ns, 4 ns, 5 ns, 6 ns, 7 ns, 8 ns, 9 ns, 10 ns, 15 ns, 20 ns, 25 ns, 30 ns, 35 ns, 40 ns, 45 ns, or 50 ns.

Integrated Monitoring System

Figure 5:
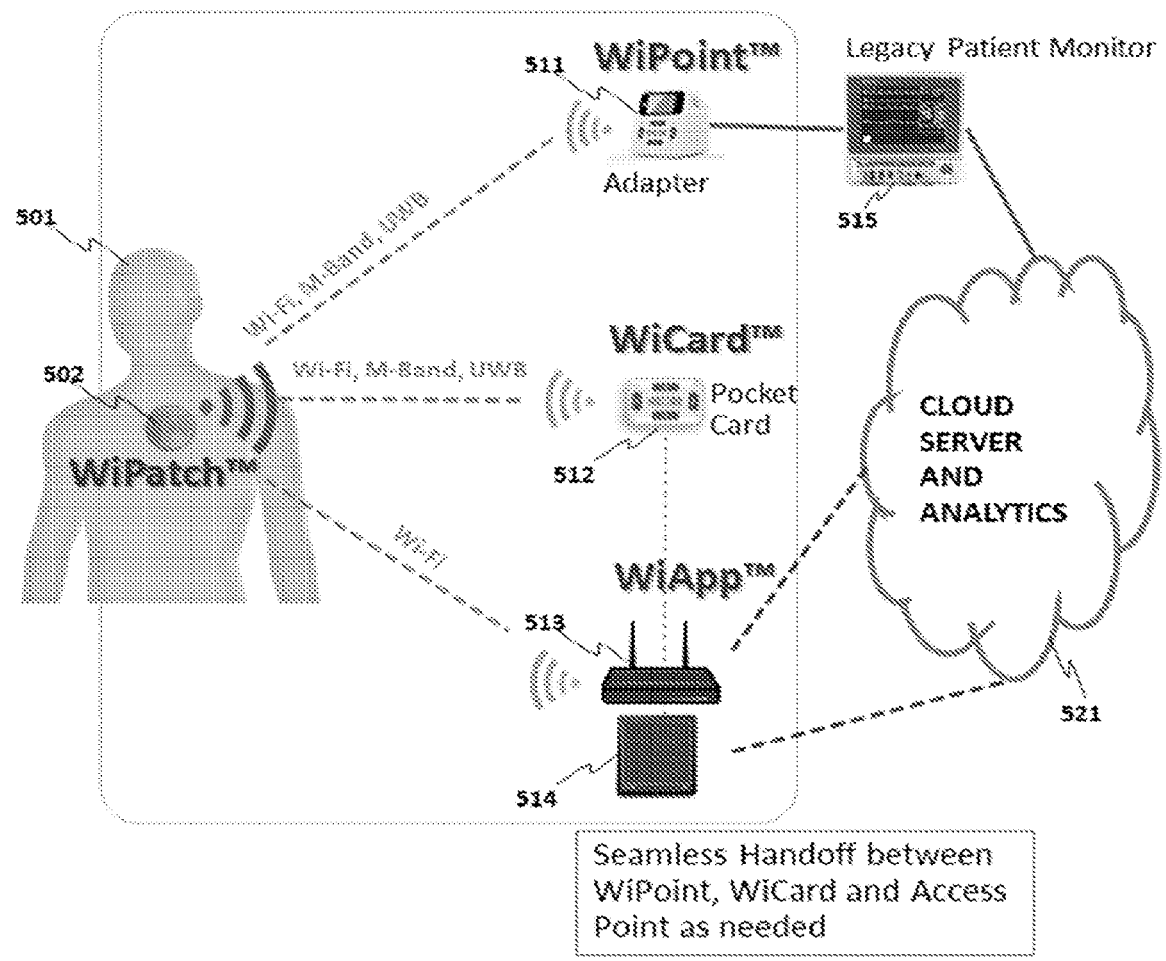
FIG. 5 shows an example of integrated monitoring system.

FIG. 5 shows an exemplary integrated monitoring system with a patch 502 and a data collection device 512. A patch 502 may be attached to a subject 501. The patch 502 may be configured to communicate with an adapter 511, a data collection device (e.g., pocket card) 512, and/or a wireless access point 513. For example, the patch may be configured to directly communicate with the adapter, data collection device, and/or wireless access point. The adapter 511 may be connected to a patient monitor 515. In some instances, the patient monitor may be a legacy patient monitor. The data collection device (e.g., pocket card) 512 may communicate with the wireless access point 513 and/or a mobile device 514. Optionally, the data collection device 512 may be configured to communicate with the adapter 511. For example, the data collection device may store data while it is operably coupled to a patch 502, allowing a user to move around freely. When desired or necessary, the data collection device may be coupled to the adapter (e.g. via a connector) and may upload the collected data such that it can be monitored or viewed on a patient monitor 515 and/or be further uploaded to a server 521. In some cases, the functionalities of the adapter, data collection device, and/or wireless access point may be portioned or differentiated. For example, the data collection device 512 may be configured to communicate directly with the patch 502 while the adapter may be configured to indirectly communicate with the patch, e.g. via the data collection device. For example, the adapter may be configured to be operably coupled to the data collection device and download relevant data from the data collection device, which may then be displayed on the patient monitor via the adapter. As another example, the adapter may be configured to be operably coupled to the data collection device and download relevant data from the data collection device, which may then be further processed or be uploaded onto a server. The wireless access point 513 and/or a mobile device 514 may communicate with a server 521 which may provide data analytics. In some instances, the adapter 511 or patient monitor 515 may communicate with a server 521 which may provide data analytics.

In some applications, an adapter 511 may be configured for in-bed monitoring, and a data collection device (e.g., pocket card) 512 may be configured for ambulatory monitoring.

A data collection device (e.g., pocket card) 512 may in some instances be similar to an adapter 511 but collapsed in a pocket size card with a rechargeable battery. For example, the data collection device may provide similar functionality (e.g., communication with a patch, data collection capabilities, data storage capabilities, capabilities to communicate with a server, etc). Alternatively, the data collection device and the adapter may provide different functionalities as discussed with respect to FIGS. 22-24. For example, the data collection device may allow a relevant data from a patch 502 to be continuously recorded while allowing a user greater freedom of movement, and the adapter may allow the relevant data to be downloaded for further utilization, e.g. viewing or analysis on a monitor 515.

A data collection device (e.g., pocket card) 512 may comprise a microphone for recording user triggered voice messages.

A data collection device (e.g., pocket card) 512 may be customizable. Examples of customization include tweaking core electronics, application software, and industrial design with appropriate user buttons, etc.

A data collection device (e.g., pocket card) 512 may capture data from a patch 502, and store and forward the data to other devices and cloud servers. A data collection device 512 may store data up to about three days. Optionally, the data collection device may allow storage of data for a period of time equal to or greater than about a day, two days, three days, four days, five days, six days, seven days, eight days, nine days, or ten days.

A data collection device (e.g., pocket card) 512 may collect generic inputs by patient. In some instances, one or more buttons may be provided on the data collection device. For example, an "event" button may be used to signal experiencing of discomfort by a user. Afterwards, monitored signals may be tagged or flagged then onwards for a period of time equal to about 1 minute, 2 minutes, 3 minutes, 4 minutes, 5 minutes, 6 minutes, 7 minutes, 8 minutes, 9 minutes, 10 minutes, 10-20 minutes, 21-30 minutes, 31-40 minutes, 41-50 minutes, or 51-60 minutes. A "message" button is used to record a brief message normally in association with the event.

A patch 502 may comprise a wireless communication unit for connection with access points. A patch 502 may further comprise a USB or a test port for testing purpose or for configuring an electronics module of the patch. A patch 502 may transfer data in a batch mode, or in a real time streaming mode.

A patch 502 may communicate simultaneously with three capture devices (511, 512, and 513) to maintain continuous monitoring. A patch 502 may periodically or randomly switch between three capture devices (511, 512, and 513) to maintain continuous monitoring. Captured signals may be timestamped in order to reconstruct data sequence at a server.

A patch 502 may be connected to adapter 511 (e.g., when in bed); such a communication may be based on Wi-Fi, M-Band, or UWB. Adapter 511 may be further connected to a legacy patient monitor 515. In addition, the legacy patient monitor 515 may connect to a cloud server 521 for analytics.

A patch 502 may be connected to a pocket device 512 (e.g., when in an ambulatory service switched by caretaker); such a communication may be based on Wi-Fi, M-Band, or UWB. A pocket device 512 may be further connected to a wireless access point 513, wherein the wireless access point 513 may transmit the signals to an analytics server 521.

A patch 502 may be connected to a Wi-Fi Access Point 513 when so chosen by caretaker; such a communication may be based on Wi-Fi, M-Band, or UWB. The wireless access point 513 may transmit the signals to an analytics server 521.

Method of Using the Technologies

The technologies disclosed herein may comprise a method using a patch. A method may be used for multi-day live monitoring where a user using the technologies may be monitored by a remote healthcare provider or a family member. In some embodiments, a method is used in an in-patient setting, where data continuously displayed on patient monitors to facilitate patient monitoring. A method can be employed in ambulatory outpatient monitoring, where ambulatory staff member can monitor physiological signals and correlate the physiological signals with symptoms. A method may be used for Holter monitoring where continuously monitoring various electrical activity of cardiovascular system can last more than 24 hours. A method may be used for event monitoring where an event is flagged either by patient or by pressing a button and few minutes of data are transmitted by patient on occurrence of an event, and loop monitor.

A method may comprise using a patch for monitoring physiological data. The method may comprise protecting a patch from an external source of electrical current. The method may comprise contacting a surface of a user with a base of the patch. The patch may comprises: one or more electrodes operably coupled to the base, the one or more electrodes configured to monitor physiological data from the user; an electronic module in communication with the one or more electrodes, the electronic module configured to receive the monitored physiological data; one or more resistors operably coupled to the one or more electrodes and/or the electronic module.

A method may comprise receiving an external source of electrical current; and protecting the patch from the external source of electrical current with aid of the one or more resistors. An external source of current may be a defibrillation voltage pulse applied to the user. The defibrillation voltage pulse may be applied to the user across the user's chest.

The one or more resistors may be configured to protect the one or more electrodes and/or the electronic module of the patch. The one or more resistors may be configured to protect a component of the patch from heat generated by the external source of electrical current. The patch further may comprise one or more batteries. The one or more resistors may be located about or more than about 1 cm from each of the one or more batteries. A number of the one or more resistors may correspond to at least a number of the one or more electrodes. Each of the one or more electrodes may be operably coupled to a corresponding resistor. The corresponding resistor may be located between each of the one or more electrodes and the electronic module. The electronic module may comprise one or more processors configured to analyze the physiological data: inferring an ECG signal, a respiratory signal, and a heart rate.

An electronic module may comprise a wireless communication means. The wireless communication means may comprise one or more of the following: a near range communication means, a short range communication means, and a long range communication means. The wireless communication means may operate on one or more of the following protocols: a Bluetooth protocol, a Wi-Fi protocol, an ultra-wide band protocol. The patch may be operably coupled to one or more sensors configured to measure additional types of physiological data.

A patch may comprise the one or more sensors. A patch may be operably coupled to the one or more sensors via wired or wireless connection. The one or more sensors comprise a respiration measurement sensor. The one or more sensors may comprise a SpO2 sensor. Each of the one or more sensors may be operably coupled to a corresponding resistor. The patch may comprise at least four electrodes comprising at least a right arm (RA), left arm (LA), right leg (RL), and left leg (LL) electrode, and the corresponding resistor may be also operably coupled to the RA and/or LL electrode. The patch may comprise four or more electrodes configured to gather information sufficient to generate at least three limb leads. The patch may comprise two or more batteries. The two or more batteries may be located between the RA and RL electrodes, and between the LA and LL electrodes. The one or more electrodes, the electronic module, and the one or more resistors may be located on a single layer.

A method for monitoring physiological data may comprise contacting a surface of a user with a base of the patch, wherein the patch comprises: (a) monitoring, with aid of one or more electrodes operably coupled to the base, the physiological data from the user; (b) receiving, at an electronic module in communication with the one or more electrodes, the monitored physiological data; and (c) transmitting the received physiological data to two or more different types of devices. The two or more different types of devices may comprise at least two of a mobile device, a data collection device, and a patient monitor. The patch may be configured to communicate with the data collection device via Wi-Fi, MBand, and/or UWB. The patch may be configured to communicate with the mobile device via Wi-Fi. The patch may be configured to communicate with the patient monitor via Wi-Fi, MBand, and/or UWB. The patch may be configured to communicate with the patient monitor with aid of an adapter. The data collection device may be further configured to communicate with the mobile device and/or the patient monitor. The patient monitor and/or mobile device may be further configured to communicate with an external server. A type of device communicating with the patch may be selected by the user. A type of device communicating with the patch may be selected by a healthcare professional. The patch may be configured to communicate with the two or more devices using different communication schemes. The patch may be configured to communicate with the two or more devices using a same communication scheme. The patch may be configured to communicate with the two or more devices as an alternative. The patch may be configured to communicate with three or more different types of devices. The three or more different types of devices may comprise a mobile device, a data collection device, and a patient monitor.

A method for monitoring physiological data may comprise monitoring the physiological data from a user; receiving the monitored physiological data from the patch, wherein the data collection device is equal to or less than 2 grams. The data collection device may comprise a maximum dimension equal to or smaller than 8 cm. The data collection device may comprise a volume equal to or smaller than 30 cm$^3$. The data collection device may be in a form of a card or in a form of a wrist band. The data collection device may comprise a memory. The data collection device may be capable of storing physiological data measured from the user for at least two days or more. The data collection device may be configured for Holter monitoring, event monitoring, and/or loop monitoring. The data collection device may be configured to store and/or transmit the received physiological data to another device or a server in real time. The data collection device may be configured to transmit the received physiological data to another device or a server after data collection may be completed. The data collection device may be configured to transmit the received physiological data to another device or a server in batch file. The data collection device may be not configured to analyze the received physiological data. The data collection device may be configured to track a location of the user. The data collection device may comprise a GPS. The data collection device may comprise a user interface. The user interface may comprise one or more buttons. Actuation of the one or more buttons may signal a beginning of an event for event monitoring. Actuation of the one or more buttons may be configured to record and store a message from the user in the data collection device with aid of a microphone. The user interface may comprise a touch-screen display. The data collection device may comprise a microphone. The data collection device may be configured to communicate with a mobile device. The mobile device may be a cellphone, a portable digital assistant (PDA), and/or a tablet. The data collection device may be configured to communicate with a patient monitor. The data collection device may be configured to communicate with the patient monitor with aid of an adapter. The data collection device may be further configured to communicate with two or more different types of devices. The two or more different types of devices may comprise a patient monitor and a mobile device. The system may further comprise a server configured to receive the physiological data, wherein the server may be configured to perform analytics on the physiological data. The data collection device may communicate with the patch via Wi-Fi, MBand, and/or UWB. The patch may be further configured to communicate with a third device. The patch may be configured to communicate with the third device via the data collection device. The data collection device may extend a communication distance for the patch to communicate with the third device. The data collection device may extend the communication distance between the patch and the third device by at least 2 times as compared to not having the data collection device.

Digital Processing Device

In some examples, the platforms, systems, media, and methods described herein may include a digital processing device, or use of the same. In some examples, the digital processing device may include one or more hardware central processing units (CPUs) or general purpose graphics processing units (GPGPUs) that carry out the device's functions. In some examples, the digital processing device may further comprise an operating system configured to perform executable instructions. The digital processing device may be optionally connected a computer network. The digital processing device may be optionally connected to the Internet such that it accesses the World Wide Web. The digital processing device may be optionally connected to a cloud computing infrastructure. The digital processing device may be optionally connected to an intranet. The digital processing device may be optionally connected to a data storage device.

In accordance with the description herein, suitable digital processing devices may include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Many smartphones may be suitable for use in the system described herein. Televisions, video players, and digital music players with optional computer network connectivity may be suitable for use in the system described herein. Suitable tablet computers may include those with booklet, slate, and convertible configurations, known to those of skill in the art.

The digital processing device may include an operating system configured to perform executable instructions. The operating system may be, for example, software, including programs and data, which manages the device's hardware and provides services for execution of applications. Suitable server operating systems may include, by way of non-limiting examples, FreeBSD, OpenBSD, NetBSD®, Linux, Apple® Mac OS X Server®, Oracle® Solaris®, Windows Server®, and Novell® NetWare®. Suitable personal computer operating systems may include, by way of non-limiting examples, Microsoft® Windows®, Apple® Mac OS X®, UNIX®, and UNIX-like operating systems such as GNU/Linux®. In some examples, the operating system may be provided by cloud computing. Suitable mobile smart phone operating systems may include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Suitable media streaming device operating systems may include, by way of non-limiting examples, Apple TV®, Roku®, Boxee®, Google TV®, Google Chromecast®, Amazon Fire®, and Samsung® HomeSync®. Suitable video game console operating systems may include, by way of non-limiting examples, Sony® P53®, Sony® PS4®, Microsoft® Xbox 360®, Microsoft Xbox One, Nintendo® Wii®, Nintendo® Wii U®, and Ouya®.

The device may include a storage and/or memory device. The storage and/or memory device may be one or more physical apparatuses used to store data or programs on a temporary or permanent basis. The device may be volatile memory and may require power to maintain stored information. The device may be non-volatile memory and retains stored information when the digital processing device is not powered. The non-volatile memory may comprise flash memory, dynamic random-access memory (DRAM), ferroelectric random access memory (FRAM), phase-change random access memory (PRAM).

The digital processing device may include a display to send visual information to a user. The display may be a cathode ray tube (CRT), a liquid crystal display (LCD), a thin film transistor liquid crystal display (TFT-LCD), an organic light emitting diode (OLED) display, a passive-matrix OLED (PMOLED) or active-matrix OLED (AMOLED) display, a plasma display, and/or a video projector.

The digital processing device may include an input device to receive information from a user. The input device may be a keyboard. The input device may be a pointing device including, by way of non-limiting examples, a mouse, trackball, track pad, joystick, game controller, or stylus. The input device may be a touch screen or a multi-touch screen. The input device may be a microphone to capture voice or other sound input. The input device may be a video camera or other sensor to capture motion or visual input. The input device may be a Kinect, Leap Motion, or the like. The input device may be a combination of devices such as those disclosed herein.

Non-Transitory Computer Readable Storage Medium

The platforms, systems, media, and methods disclosed herein may include one or more non-transitory computer readable storage media encoded with a program including instructions executable by the operating system of an optionally networked digital processing device. A computer readable storage medium may be a tangible component of a digital processing device. A computer readable storage medium is optionally removable from a digital processing device. A computer readable storage medium includes, by way of non-limiting examples, CD-ROMs, DVDs, flash memory devices, solid state memory, magnetic disk drives, magnetic tape drives, optical disk drives, cloud computing systems and services, and the like. In some cases, the program and instructions are permanently, substantially permanently, semi-permanently, or non-transitorily encoded on the media.

Computer Program

In some embodiments, the platforms, systems, media, and methods disclosed herein may include at least one computer program, or use of the same. A computer program includes a sequence of instructions, executable in the digital processing device's CPU, written to perform a specified task. Computer readable instructions may be implemented as program modules, such as functions, objects, Application Programming Interfaces (APIs), data structures, and the like, that perform particular tasks or implement particular abstract data types. In light of the disclosure provided herein, a computer program may be written in various versions of various languages.

Web Application

A computer program may include a web application. In light of the disclosure provided herein, a web application may utilize one or more software frameworks and one or more database systems. A web application may be created upon a software framework such as Microsoft® .NET or Ruby on Rails (RoR). A web application may utilize one or more database systems including, by way of non-limiting examples, relational, non-relational, object oriented, associative, and XML database systems. In further embodiments, suitable relational database systems include, by way of non-limiting examples, Microsoft® SQL Server, mySQL™, and Oracle®. Those of skill in the art will also recognize that a web application, in various embodiments, is written in one or more versions of one or more languages. A web application may be written in one or more markup languages, presentation definition languages, client-side scripting languages, server-side coding languages, database query languages, or combinations thereof. In some embodiments, a web application is written to some extent in a markup language such as Hypertext Markup Language (HTML), Extensible Hypertext Markup Language (XHTML), or eXtensible Markup Language (XML). A web application may be written to some extent in a presentation definition language such as Cascading Style Sheets (CSS). A web application may be written to some extent in a client-side scripting language such as Asynchronous Javascript and XML (AJAX), Flash® Actionscript, Javascript, or Silverlight®. A web application may be written to some extent in a server-side coding language such as Active Server Pages (ASP), ColdFusion®, Perl, Java™ JavaServer Pages (JSP), Hypertext Preprocessor (PHP), Python™, Ruby, Tcl, Smalltalk, WebDNA®, or Groovy. A web application may be written to some extent in a database query language such as Structured Query Language (SQL).

Mobile Application

A computer program may include a mobile application provided to a mobile digital processing device. The mobile application may be provided to a mobile digital processing device at the time it is manufactured. The mobile application may be provided to a mobile digital processing device via the computer network described herein.

A mobile application may be created, for example, using hardware, languages, and development environments. Mobile applications may be written in various programming languages. Suitable programming languages include, by way of non-limiting examples, C, C++, C#, Objective-C, Java™, Javascript, Pascal, Object Pascal, Python™, Ruby, VB.NET, WML, and XHTML/HTML with or without CSS, or combinations thereof.

Suitable mobile application development environments are available from several sources. Commercially available development environments include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Several commercial forums may be available for distribution of mobile applications including, by way of non-limiting examples, Apple® App Store, Android™ Market, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

A computer program may include a standalone application, which is a program that is run as an independent computer process, not an add-on to an existing process, e.g., not a plug-in. Standalone applications may be compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program.

Web Browser Plug-in

The computer program may include a web browser plug-in. In computing, a plug-in may be one or more software components that add specific functionality to a larger software application. Makers of software applications support plug-ins to enable third-party developers to create abilities which extend an application, to support easily adding new features, and to reduce the size of an application. When supported, plug-ins may enable customizing the functionality of a software application. For example, plug-ins are commonly used in web browsers to play video, generate interactivity, scan for viruses, and display particular file types. Web browser plug-ins include, without limitation, Adobe® Flash® Player, Microsoft® Silverlight®, and Apple® QuickTime®. The toolbar may comprise one or more web browser extensions, add-ins, or add-ons. In some embodiments, the toolbar comprises one or more explorer bars, tool bands, or desk hands.

Several plug-in frameworks may be available that may enable development of plug-ins in various programming languages, including, by way of non-limiting examples, C++, Delphi, Java™, PHP, Python™, and VB .NET, or combinations thereof.

Web browsers (also called Internet browsers) are software applications, which may be configured for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called mircrobrowsers, mini-browsers, and wireless browsers) may be configured for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

The systems, media, networks and methods described herein may include software, server, and/or database modules, or use of the same. Software modules may be created using various machines, software, and programming languages. The software modules disclosed herein are implemented in a multitude of ways. A software module may comprise a file, a section of code, a programming object, a programming structure, or combinations thereof. A software module may comprise a plurality of files, a plurality of sections of code, a plurality of programming objects, a plurality of programming structures, or combinations thereof. The one or more software modules may comprise, by way of non-limiting examples, a web application, a mobile application, and a standalone application. In some embodiments, software modules are in one computer program or application. Software modules may be in more than one computer program or application. Software modules may be hosted on one machine. Software modules may be hosted on more than one machine. Software modules may be hosted on cloud computing platforms. Software modules may be hosted on one or more machines in one location. Software modules may be hosted on one or more machines in more than one location.

Databases

The platforms, systems, media, and methods disclosed herein may include one or more databases, or use of the same. In view of the disclosure provided herein, many databases are suitable for storage and retrieval of physiological data. In various embodiments, suitable databases include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. A database may be web-based. A database may be cloud computing-based. A database may be based on one or more local computer storage devices.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein may be employed in practicing the disclosure.

What is claimed is:

1. A patch for monitoring physiological data, comprising:
(a) a base configured to come in contact with a surface of a user;
(b) one or more electrodes operably coupled to the base, the one or more electrodes configured to collect the physiological data from the user;
(c) an electronic module in communication with the one or more electrodes, wherein the electronic module is configured to receive the collected physiological data;
(d) one or more resistors operably coupled to the one or more electrodes and/or the electronic module, wherein the one or more resistors are configured to reduce a voltage shock generated by an external source of electrical current;
(e) a battery, wherein the battery comprises a positive terminal and a negative terminal, and the battery is associated with a battery voltage;
(f) at least two diodes configured to be coupled back to back to form a safety diode assembly, wherein a first diode of the at least two diodes is configured to couple to the positive terminal of the battery, and a second diode of the at least two diodes is configured to couple to the negative terminal of the battery, wherein the safety diode assembly is configured to further reduce the voltage shock by rectifying a voltage pulse to the battery voltage.

2. The patch of claim 1, wherein the at least two diodes are configured to have a switching and recovery time under 5 ns.

3. The patch of claim 1, wherein the one or more resistors are further configured to reduce heat generated by the external source of electrical current.

4. The patch of claim 1, wherein a resistance of each of the one or more resistors is more than 20 k ohms.

5. The patch of claim 1, wherein the patch further comprises one or more batteries, and wherein the one or more additional resistors are located more than 1 cm from each of the one or more additional batteries.

6. The patch of claim 1, wherein a number of the one or more resistors is greater than a number of the one or more electrodes.

7. The patch of claim 1, wherein each of the one or more electrodes is operably coupled to a corresponding resistor of the one or more resistors.

8. The patch of claim 1, wherein the electronic module comprises one or more processors configured to analyze the physiological data to infer one or more of an ECG signal, respiratory signal, and heart rate.

9. The patch of claim 1, wherein the electronic module comprises a wireless communication means.

10. The patch of claim 1, wherein the patch is less than about 1 inch thick.

11. The patch of claim 1, wherein the one or more electrodes comprises at least four electrodes comprising at least a right arm (RA), left arm (LA), right leg (RL), and left leg (LL) electrode.

12. The patch of claim 1, wherein the one or more electrodes, the electronic module, the battery, and the one or more resistors are located on a single layer.

13. A system for monitoring physiological data, comprising:
the patch of claim 1, one or more sensors configured to measure additional types of physiological data, wherein the patch is operably coupled to the one or more sensors.

14. The system of claim 13, wherein each of the one or more sensors is operably coupled to a corresponding resistor the patch.

15. The system of claim 13, wherein the one or more electrodes comprises at least four electrodes comprising at least a right arm (RA), left arm (LA), right leg (RL), and left leg (LL) electrode, and a resistor of the one or more resistors is operably coupled to the RA and/or LL electrode.

* * * * *